US010765453B2

United States Patent
Kim

(10) Patent No.: US 10,765,453 B2
(45) Date of Patent: Sep. 8, 2020

(54) DEVICE AND METHOD FOR TREATING OSTEONECROSIS

(71) Applicant: Texas Scottish Rite Hospital for Children, Dallas, TX (US)

(72) Inventor: Harry K. W. Kim, Dallas, TX (US)

(73) Assignee: Texas Scottish Rite Hospital for Children, Dallas, TX (US)

( * ) Notice: Subject to any disclaimer, the term of this patent is extended or adjusted under 35 U.S.C. 154(b) by 0 days.

(21) Appl. No.: 15/956,245

(22) Filed: Apr. 18, 2018

(65) Prior Publication Data

US 2018/0296244 A1   Oct. 18, 2018

Related U.S. Application Data

(63) Continuation-in-part of application No. 15/490,595, filed on Apr. 18, 2017.

(51) Int. Cl.
*A61B 17/34* (2006.01)
*A61B 17/17* (2006.01)
(Continued)

(52) U.S. Cl.
CPC ...... *A61B 17/3472* (2013.01); *A61B 17/1622* (2013.01); *A61B 17/1664* (2013.01); *A61B 17/1668* (2013.01); *A61B 17/1697* (2013.01); *A61B 17/17* (2013.01); *A61B 17/1714* (2013.01); *A61B 17/1721* (2013.01); *A61B 17/1725* (2013.01); *A61B 17/1764* (2013.01); *A61M 3/022* (2014.02); *A61M 3/0204* (2014.02); *A61M 3/0212* (2014.02); *A61B 17/1628* (2013.01); *A61B 17/1739* (2013.01); *A61B 17/3403* (2013.01); *A61B 90/50* (2016.02); *A61B 90/57* (2016.02);
(Continued)

(58) Field of Classification Search
CPC . A61B 17/17; A61B 17/1714; A61B 17/1725; A61B 17/1764; A61B 17/1664; A61B 17/1668; A61B 17/3472; A61B 17/8805; A61B 17/8833; A61B 17/7097; A61B 2217/007
See application file for complete search history.

(56) References Cited

U.S. PATENT DOCUMENTS 5,437,683 A    8/1995  Neumann et al.
8,303,594 B2  11/2012  Lynch et al.
(Continued)

OTHER PUBLICATIONS

International Search Report and Written Opinion of USPTO for PCT/US2018/028137 dated Aug. 9, 2018, 15 pp.

*Primary Examiner* — Nathan R Price
*Assistant Examiner* — Anh Bui
(74) *Attorney, Agent, or Firm* — Edwin S. Flores; Chalker Flores, LLP

(57) ABSTRACT

The present invention includes a method and devices for treating osteonecrosis in, e.g., children, adolescents, and adults comprising: identifying a subject in need of treatment for osteonecrosis; drilling two or more holes into a bone in need of treatment for osteonecrosis; inserting two or more needles or cannulas into the holes in the bone; washing an interior of the bone with a washing fluid introduced through one or more of the needles or cannulas inserted into the bone; and after washing the interior of the bone introducing one or more bone growth promoting materials or cells into the bone.

12 Claims, 23 Drawing Sheets

(51) Int. Cl.
  *A61B 17/16*   (2006.01)
  *A61M 3/02*    (2006.01)
  *A61B 90/00*    (2016.01)
  *A61B 17/00*    (2006.01)
  *A61B 90/57*    (2016.01)
  *A61M 3/00*     (2006.01)
  *A61B 90/50*    (2016.01)

(52) U.S. Cl.
  CPC .............. *A61B 2017/00477* (2013.01); *A61B 2017/00893* (2013.01); *A61B 2017/3405* (2013.01); *A61B 2017/347* (2013.01); *A61B 2090/062* (2016.02); *A61B 2217/007* (2013.01); *A61M 3/00* (2013.01); *A61M 2210/02* (2013.01)

(56) References Cited

U.S. PATENT DOCUMENTS

| | | |
|---|---|---|
| 8,328,762 B2 | 12/2012 | Woehr et al. |
| 9,138,317 B2 | 9/2015 | McGee |
| 9,550,010 B2 | 1/2017 | Schulz et al. |
| 2005/0177171 A1 | 8/2005 | Wetzler et al. |
| 2008/0103506 A1* | 5/2008 | Volpi ................. A61B 17/1714 606/96 |
| 2010/0191195 A1* | 7/2010 | Kirschenbaum ... A61B 17/1604 604/272 |
| 2011/0087161 A1 | 4/2011 | Lidgren et al. |
| 2013/0066261 A1 | 3/2013 | Henniges et al. |
| 2013/0110112 A1 | 5/2013 | Lehenkari et al. |
| 2014/0088551 A1 | 3/2014 | Vad et al. |
| 2015/0044179 A1 | 2/2015 | Saeki |
| 2017/0197017 A1 | 7/2017 | Martin et al. |

\* cited by examiner

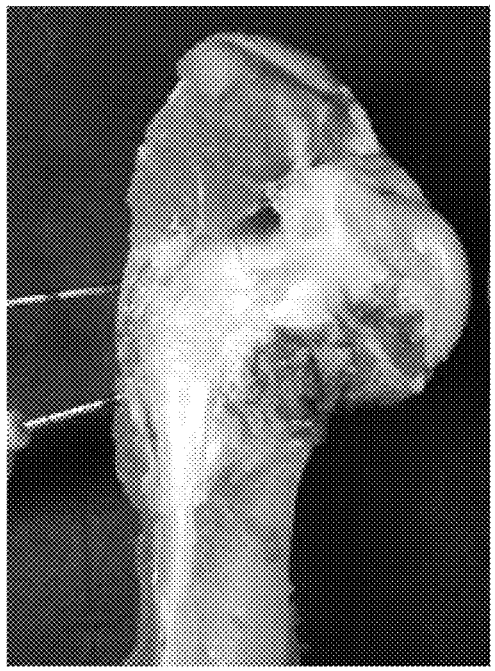
FIG. 1A  FIG. 1B
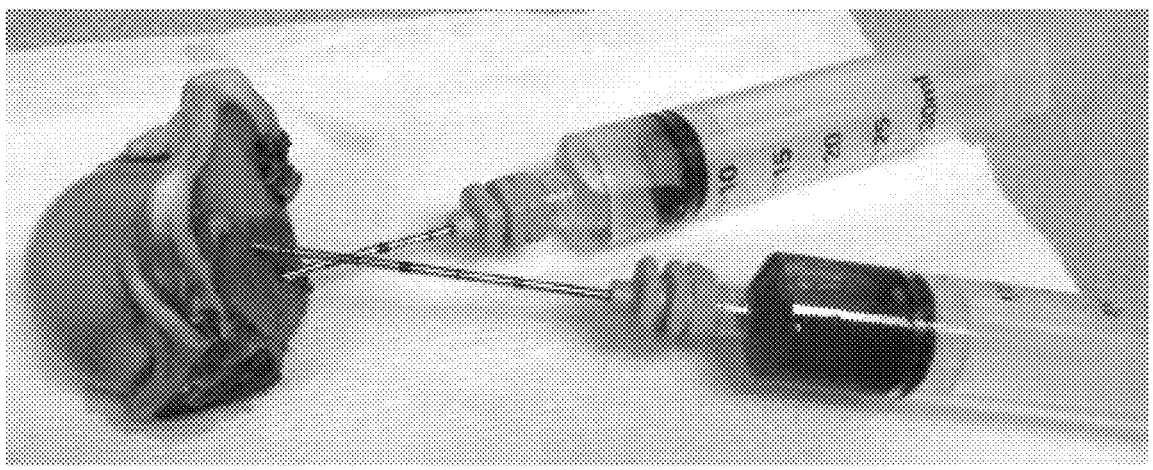
FIG. 2

Tube  1      3      5      7    Saline

Low magnification

Higher magnification

Unwashed
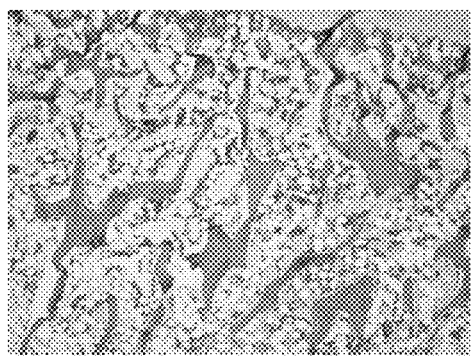
4x
Washed
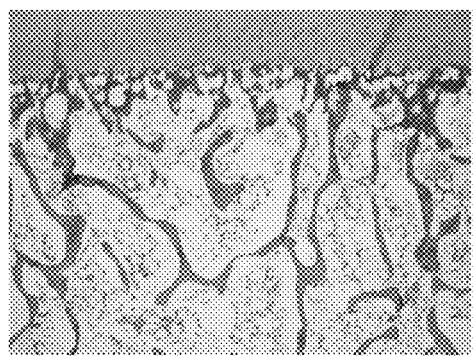
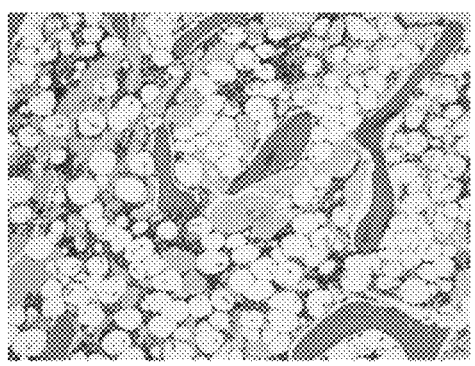
10x
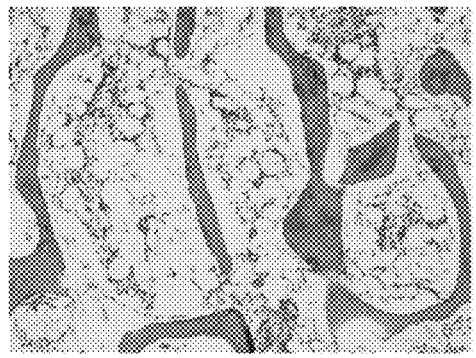
FIG. 6A
FIG. 6B
Control
No wash
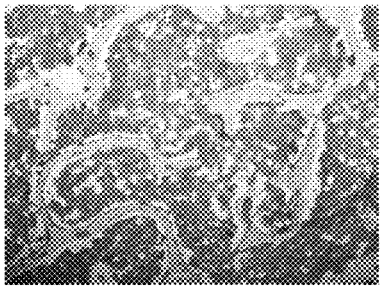
FIG. 7A
Saline Wash
(180 ml)
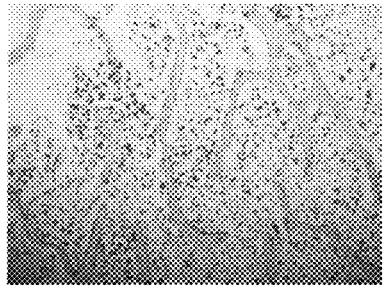
FIG. 7B
Ethanol 100% (60 ml) +
Saline 120 ml Wash
FIG. 7C Single Needle
No wash Four Needles
Washed

DEVICE AND METHOD FOR TREATING OSTEONECROSIS

CROSS-REFERENCE TO RELATED APPLICATIONS

This application is a continuation-in-part application of U.S. patent application Ser. No. 15/490,595 filed on Apr. 18, 2017 and entitled "Device and Method for Treating Osteonecrosis," the contents of which are incorporated by reference in their entirety.

STATEMENT OF FEDERALLY FUNDED RESEARCH

None.

TECHNICAL FIELD OF THE INVENTION

The present invention relates in general to the field of osteonecrosis, and more particularly, to a novel device and method for treating osteonecrosis, such as Legg-Calve-Perthes disease or adult osteonecrosis.

BACKGROUND OF THE INVENTION

Without limiting the scope of the invention, its background is described in connection with tissue regeneration.

One such method is taught in U.S. Pat. No. 9,138,317, issued to McGee, entitled "Conduits for enhancing tissue regeneration", which is said to teach apparatuses, systems, and methods for enhancing bone or soft tissue regeneration. For example, a conduit, having one or more segments, can originate at a tissue regeneration site and can have a first opening to promote physiological signals to enter the conduit and transit to a second opening that penetrates a histologically rich source of multipotent mesenchymal cells, promoting the multipotent mesenchymal cells to produce tissue regeneration response products, the response products transiting through the second opening to egress at the first opening of the conduit, and promoting tissue regeneration at the tissue regeneration site.

Another such method is taught in U.S. Pat. No. 8,382,762, issued to Brannon, entitled "Endoscopic bone debridement", which is said to teach an osteoendoscopic cylinder for tamponading bleeding along a longitudinal canal surface of an osteocentral canal of a femoral neck so as to allow endoscopic visualization of a segment of osteonecrotic bone within a femoral head. The osteoendoscopic cylinder is of a dimension adapted to receive an endoscope therein and includes an inner visual surface and an outer bony contact surface. An orientation mark along the inner visual surface is of a size and dimension to ensure a first visualization thereof with the endoscope.

SUMMARY OF THE INVENTION

In one embodiment, the present invention includes a method of treating osteonecrosis comprising: identifying a subject in need of treatment for osteonecrosis; drilling two or more holes into a bone in need of treatment for osteonecrosis; inserting two or more needles or cannulas into the holes in the bone; washing an interior of the bone with a washing fluid introduced through one or more of the needles or cannulas inserted into the bone; and after washing the interior of the bone introducing one or more bone growth promoting materials into the bone. In one aspect, the washing fluid is a biocompatible isotonic fluid and optionally comprises biocompatible detergents, biocompatible surfactants, biocompatible alcohols, antibiotics, preservatives, or combinations thereof. In another aspect, the method further comprises injecting the washed bone with at least one of autologous bone marrow, autologous bone stem cells, bone growth material, bone graft material, bone void filler, cancellous bone graft or fragments, hydrogels, gelatins, osteoconductive material, osteoproliferative material, osteoinductive material, a bone morphogenic cytokine, bone morphogenic protein, a bone morphogenic protein-2 (BMP-2), bone material infused collagen matrix, or bone morphogenic protein infused collagen matrix. In another aspect, the method further comprises washing the interior of the bone until the washing fluid is clear. In another aspect, the bone is a femoral head, a humeral head, a knee condyle, or an ankle talus. In another aspect, the washing fluid cleans at least 50, 60, 70, 75, 80, 85, or 90% of the volume within the bone. In another aspect, the method further comprises measuring the amount of cell debris and fat in the washing fluid and washing until the amount of cell debris and fat in the washing fluid is minimized. In another aspect, the method further comprises injecting the washing fluid through a first needle or cannula and drawing the washing fluid out of a second needle or cannula. In another aspect, the surgical instrument further comprises washing fluid is introduced and drawn with a syringe attached to the needle or cannula.

In another embodiment, the present invention includes a method of treating Legg-Calvé-Perthes Disease comprising: identifying a subject in need of treatment for Legg-Calvé-Perthes Disease; drilling two or more holes into a femoral head; inserting two or more needles or cannulas into the femoral head; washing an interior of the femoral head with a washing fluid introduced through one or more of the needles or cannulas drilled into the femoral head; and after washing the interior of the femoral head introducing a bone growth promoting material into the femoral head. In one aspect, the method further comprises washing fluid is a biocompatible isotonic fluid and optionally comprises biocompatible detergents, biocompatible surfactants, biocompatible alcohols, antibiotics, preservatives, or combinations thereof. In another aspect, the subject is a pediatric, an adolescent, or an adult. In another aspect, the femoral head osteonecrosis is idiopathic (unknown cause) or due to corticosteroid, trauma, alcohol, sickle cell disease, or other known causes of osteonecrosis. In another aspect, the method further comprises injecting the washed bone with at least one of autologous bone marrow, autologous bone stem cells, bone growth material, bone graft material, bone void filler, cancellous bone graft or fragments, hydrogels, gelatins, osteoconductive material, osteoproliferative material, osteoinductive material, a bone morphogenic cytokine, bone morphogenic protein, a bone morphogenic protein-2 (BMP-2), bone material infused collagen matrix, or bone morphogenic protein infused collagen matrix. In another aspect, the method further comprises washing the interior of the femoral head until the washing fluid is clear before injecting the bone growth promoting material into the femoral head. In another aspect, the washing fluid cleans at least 50, 60, 70, 75, 80, 85, or 90% of the volume within the femoral head. In another aspect, the method further comprises measuring the amount of cell debris and fat in the washing fluid and washing until the amount of cell debris and fat in the washing fluid is minimized. In another aspect, the method further comprises washing fluid through a first needle or cannula and drawing the washing fluid out of a second needle or cannula. In another aspect, the washing fluid is introduced into the femoral head and drawn from the femoral head with a syringe attached to the needle or cannula.

Yet another embodiment of the present invention includes a surgical instrument comprising: a first and a second drill bit capable of drilling into a femoral head, a humeral head, a knee condyle, or an ankle talus, wherein the first and second drills create adjacent holes in the femoral head, the humeral head, the knee condyle, or the ankle talus; one or more motors attached to and capable of rotating the first and second drill bits; a handle to control the direction of the first and second drill bits; and an on/off switch connected to the motor. In one aspect, at least one of the drill bits is defined further as a needle or cannula. In another aspect, the one or more motors are electrical, mechanical, pneumatic, hydraulic, or combinations thereof. In another aspect, the surgical instrument further comprises one or more gears between the one or more motors and the two or more drills that at least one of: increase or decrease the speed of the two or more drills, or increase or decrease the torque of the two or more drills. In another aspect, the apparatus further comprises one or more drill chucks capable of holding drills of different sizes. In another aspect, the on/off switch is a variable speed switch. In another aspect, the apparatus further comprises a cam that provides a hammer action, a rotary action, or both a rotary and hammer action, to the two or more drill bits. In another aspect, the drill bits or the apparatus is disposable. In another aspect, the subject is a pediatric, an adolescent, or an adult. In another aspect, the femoral head osteonecrosis is idiopathic (unknown cause) or due to corticosteroid, trauma, alcohol, sickle cell disease, or other known causes of osteonecrosis. In another aspect, the surgical instrument further comprises a drill press mechanism at least one of: increases the control by a user, increases a leverage of a user, or is adjustable to increase or decrease an angle between the two or more drill bits to compensate for the size of the femoral head, wherein the drill press is angled to direct the two or more drill bits into a region at or below the greater trochanter or humerus metaphysis, through a neck of the femur or humerus, and into the femoral or humeral head. In another aspect, the surgical instrument further comprises one or more sleeves or tubes surrounding the two or more drill bits, wherein the sleeves are adapted to remain after the drills have been removed from the femoral head to at least one of: facilitate the washing of the femoral head, or introduce bone growth promoting agents into the femoral head. In another aspect, the one or more drill bits are internally cooled. In another aspect, the one or more drill bits comprise a slow spiral, a standard spiral, a quick spiral, a worm spiral, two or more flutings, a split point, or a step tip. In another aspect, the surgical instrument further comprises a drill guide that controls the direction of the two or more drill bits, wherein the drill guide is adapted to be affixed to a skin adjacent the femoral head, wherein openings in the drill guide are aligned with a greater trochanter, a neck of the femur, and the femoral head.

In yet another embodiment, the present invention includes a drill guide that controls the direction of the two or more drill bits, comprising: two or openings in the drill guide are aligned with a greater trochanter, a neck of the femur, and the femoral head; and a skin attachment mechanism, wherein the skin attachment mechanism affixes, at least temporarily, the drill guide in communication with the greater trochanter, the neck of the femur, and the femoral head. In one aspect, the skin attachment mechanism is an adhesive, a pin or pins, and/or one or more suction cups. In another aspect, the skin attachment mechanism is an arm of an apparatus controllable in an x-y, a y-z, an x-z, or an x-y-z axis.

In one embodiment, the present invention includes a surgical instrument including: a handle; a central stationary assembly coupled to the handle, including a first guide cannula, a clamping mechanism, a first depth adjustment, and a first protractor arm component; a first needle assembly disposed to be inserted into the first guide cannula and including a first needle assembly cannula, a first drilling assembly disposed to be inserted in the first needle cannula assembly, and a first locking mechanism disposed to engage the first drill assembly; an adjustable subassembly disposed to be rotatably coupled to the central stationary assembly and including a second guide cannula disposed to engage the clamping mechanism, a second depth adjustment, and a second protractor arm component disposed to slidably engage the first protractor arm component; and a second needle assembly disposed to be inserted into the second guide cannula and including a second needle assembly cannula, a second drilling assembly disposed to be inserted in the second needle assembly cannula, and a second locking mechanism disposed to engage the second drilling assembly. In one aspect, the first locking mechanism includes a first luer lock and a first luer lock collar disposed to engage the first luer lock. In another aspect, the second locking mechanism includes a second luer lock and a second lock collar disposed to engage the second luer lock. In another aspect, the first locking mechanism includes a first luer lock and a first drill interface disposed to rotatably engage the first luer lock. In another aspect, the second locking mechanism includes a second luer lock and a second drill interface disposed to rotatably engage the second luer lock. In another aspect, the clamping mechanism includes a guide clamp disposed to engage the second guide cannula, a tension clamp, and a tension clamp lever. In another aspect, the first protractor arm component is disposed to slide on or within the second protractor arm component to position a first tip of the first needle assembly relative to a second tip of the second needle assembly when the first needle assembly is inserted into the first guide cannula and the second needle assembly is inserted into the second guide cannula.

In another embodiment, the present invention includes a method of treating an osteonecrosis including: identifying a subject in need of treatment for osteonecrosis; positioning a needle targeting guide to drill a first hole into a bone in need of treatment for osteonecrosis, the needle targeting device including a first needle assembly, wherein the first needle assembly includes a removable first drilling assembly, a second needle assembly, wherein the second needle assembly includes a second removable drilling assembly; drilling the first hole in the bone with the first drilling assembly of the first needle assembly; positioning the needle targeting guide to drill a second hole in the bone, by rotating the needle targeting guide about a longitudinal axis of the first needle assembly or by adjusting a position of a tip of the second needle assembly relative to a position of a tip of the second needle assembly; drilling the second hole with the second needle assembly; withdrawing the drill assembly from the first needle assembly or from the second needle assembly; and washing an interior of the bone with a washing fluid introduced through the first needle assembly or through the second needle assembly. In one aspect, the method further includes introducing one or more bone growth promoting materials into the bone through the first needle assembly or through the second needle assembly. In another aspect, the needle targeting device further includes:

a handle; a central stationary assembly coupled to the handle, including a first guide cannula, a clamping mechanism, a first depth adjustment, and a first protractor arm component; and an adjustable subassembly disposed to be rotatably coupled to the central stationary assembly and including a second guide cannula disposed to engage the clamping mechanism, a second depth adjustment, and a second protractor arm component disposed to slidably engage the first protractor arm component; wherein the first needle assembly is disposed to be inserted into the first guide cannula and includes a first needle assembly cannula, and a first locking mechanism disposed to engage the first drilling assembly, and wherein the first drilling assembly is disposed to be inserted in the first needle assembly cannula; and wherein the second needle assembly is disposed to be inserted into the second guide cannula and includes a second needle assembly cannula, and a second locking mechanism disposed to engage the second drilling assembly, and wherein the second drilling assembly is disposed to be inserted in the second needle assembly cannula.

In another embodiment, the present invention includes a surgical instrument including: a frame with one or more locking pins disposed within the frame, wherein the frame is configured to receive a first guide cannula and a second guide cannula; a first guide cannula and a second guide cannula, wherein the first guide cannula and the second guide cannula are disposed to be inserted into the frame and locked into place with the one or more locking pins; a first needle assembly disposed to be inserted into the first guide cannula and including a first needle assembly cannula, a first drilling assembly disposed to be inserted in the first needle cannula assembly, and a first locking mechanism disposed to engage the first drill assembly; a second needle assembly disposed to be inserted into the second guide cannula and including a second needle assembly cannula, a second drilling assembly disposed to be inserted in the second needle assembly cannula, and a second locking mechanism disposed to engage the second drilling assembly. In one aspect, the first locking mechanism includes a first luer lock and a first luer lock collar disposed to engage the first luer lock. In another aspect, the second locking mechanism includes a second luer lock and a second luer lock collar disposed to engage the second luer lock. In another aspect, the first locking mechanism includes a first luer lock and a first drill interface disposed to rotatably engage the first luer lock. In another aspect, the second locking mechanism includes a second luer lock and a second drill interface disposed to rotatably engage the second luer lock. In another embodiment, the present invention includes a method of treating an osteonecrosis including identifying a subject in need of treatment for osteonecrosis; positioning a first guide cannula; positioning a first needle assembly with the first guide cannula to drill a first hole into a bone in need of treatment for osteonecrosis, wherein the first needle assembly includes a removable first drilling assembly; drilling the first hole in the bone with the first drilling assembly of the first needle assembly; securing a needle targeting guide to the first guide cannula; positioning the second guide cannula using the needle targeting guide; positioning a second needle assembly with the second guide cannula to drill a second hole into the bone, wherein the second needle assembly includes a second removable drilling assembly; drilling the second hole in the bone with the second drilling assembly of the second needle assembly; withdrawing the drill assembly from the first needle assembly or from the second needle assembly; and washing an interior of the bone with a washing fluid introduced through the first needle assembly or through the second needle assembly. In one aspect, the method further includes introducing one or more bone growth promoting materials into the bone through the first needle assembly or through the second needle assembly.

BRIEF DESCRIPTION OF THE DRAWINGS

For a more complete understanding of the features and advantages of the present invention, reference is now made to the detailed description of the invention along with the accompanying figures and in which:

FIGS. 1A and 1B show a photograph (FIG. 1A) and a matching radiograph (FIG. 1B) of a humeral head into which two needles or cannulas are inserted of the present invention.

FIG. 2 shows a femoral head into which two needles or cannulas are inserted and are connected to syringes, the top syringe having a clear washing fluid, and the bottom syringe showing cell debris and fat in the washing fluid after traversing the femoral head.

FIGS. 6A and 6B each show the histology at a low (4×) and a high (10×) magnification of the unwashed femoral head (FIG. 6A) and the washed femoral head (FIG. 6B) according to the present invention.

FIGS. 7A to 7C show the histology of the femoral head without (FIG. 7A), with a saline wash (FIG. 7B) and with an ethanol and saline wash (FIG. 7C) to remove fat and cell debris.

DETAILED DESCRIPTION OF THE INVENTION

Figure 3A:
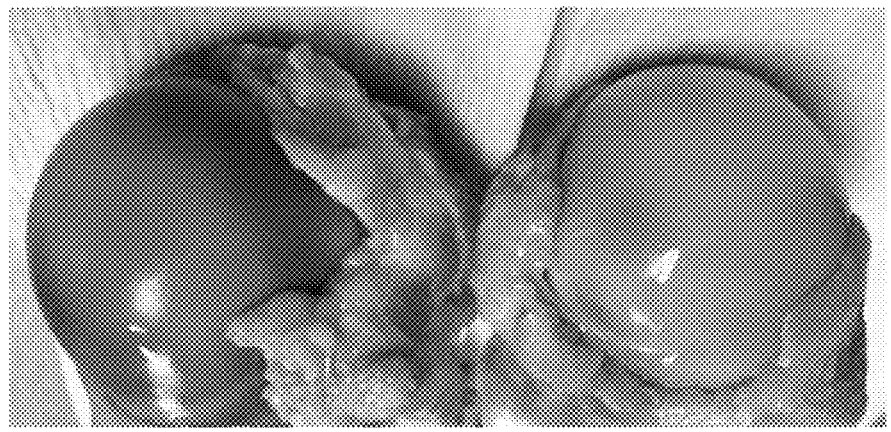
FIG. 3A shows on the left an unwashed femoral head, and the right a washed femoral head using the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

New Necrotic Bone Washing Technique.

The bone washing technique of the present invention involves placement of two or more intra-osseous needles or cannulas into pediatric or adult femoral heads for treatment of avascular necrosis (AVN) or osteonecrosis. This technique permits inflow and outflow of washing solution through the needle(s) or cannula(s) to remove, e.g., dead cell debris, necrotic marrow fat, and/or inflammatory factors. It is demonstrated herein that the removal of dead cell debris, necrotic marrow fat, and/or inflammatory factors from the marrow space significantly improves bone healing and creates space for the injection or infusion of biological therapeutic agents and/or stem cells.

Briefly, two or more intra-osseous needles and/or cannulas are placed 5-15 mm apart depending on the necrotic bone volume and the size of the femoral head. Either trans-articular (through the joint and articular cartilage) or trans-physeal/metaphyseal (starting from region below the greater trochanter) or combination needle placement technique can be used. The needles are most often inserted under fluoroscopic guidance and a specialized needle placement device may be used to facilitate the placement of the needles. The present invention can be used in a wide variety of locations that includes osteonecrosis, e.g., the femoral head, the humeral head, the knee condyle, or the ankle talus.

After the placement of two or more intra-osseous needles and/or cannulas within the necrotic bone, aspiration (negative pressure), injection/infusion (positive pressure), and/or a combination of both, are used to provide a high volume of washing solution to flow through the necrotic femoral head to remove the dead cell debris. A high volume washing of the necrotic bone can be facilitated by using a mechanical device or a pump. The amount of volume required for washing or the termination of the washing technique can be determined by assessing the clarity/turbidity of the outflow solution. Further assessment of the outflow solution can be done by measuring levels of specific inflammatory factors using visual, qualitative and/or quantitative assays.

The needles and/or cannulas will generally have following specifications: (1) 6, 7, 8, 9, 10, 11, 12, 13, 14, 15, or 6-15 gauge in diameter, depending on the size of the femoral head and the bone necrosis; (2) the tip of the needle should be less than 3.0 mm long to avoid unintentional penetration through the femoral head, but can be 8, 9, 10, 12, 15, 20, 25, 30 or more centimeters, e.g., 10 to 30 cm; and/or (3) the needle may have one or more fenestrations near the tip to increase the distribution and collection of bone washing solution.

A wide variety of washing solutions and combinations of solutions are contemplated for use with the present invention. The washing solution can be based on saline, various concentrations of ethanol, and/or include one or more biocompatible detergent and/or surfactants for removing/extracting cell debris, necrotic fat, or the necrotic extracellular matrix. The washing solution may also include antibiotics or other antimicrobial agents. The washing solution may also contain one or more bioactive agents, enzymes, or nanoparticles that facilitate the removal of the necrotic fat and the extracellular matrix in the necrotic bone marrow. The washing solution may also contain drugs or agents that stimulate angiogenesis (for instance by activation of hypoxia inducible factor-1 and vascular endothelial growth factor pathways) or stimulate osteogenesis (for instance through Wnt and/or BMP signaling pathways).

Generally, the temperature of wash solution should be warmed up to the body temperature to be physiological and more effective in removing cell debris.

Example 2. New Stem Cell or Bone Active Agent Delivery Technique

The bone delivery technique involves placement of two or more intra-osseous needles and/or cannulas into pediatric or adult femoral heads for treatment of avascular necrosis (AVN) or osteonecrosis. This technique can be used with or without first performing the bone washing technique outlined above. The use of two or more intra-osseous delivery needles and/or cannulas improves the local distribution of stem cells or bone active agents in the necrotic femoral head by subdividing the total volume of cells or bone active agents to be injected into multiple sites. The technique also improves the local retention of stem cells or bone active agents by decreasing the backflow pressure, unlike the single needle delivery technique where the total volume of injectant is delivered through a single needle site.

This technique can be used to inject cells or bone active agents alone or in combination with a delivery/carrier agent such as hydrogel or gelatin, which can be chemically designed to improve the retention of stem cells and growth factors such as bone morphogenetic proteins (BMPs).

The use of two or more needles and/or cannulas also permits two-step preparation of the necrotic bone for the delivery of stem cells or bone active agents. In the first step, a bone washing and preparation solution will be used to remove the cell debris and to distribute a chemical or catalyst required for a chemical reaction which will improve the local retention of a delivery agent and a growth factor when they are injected or infused in the second step.

The needle and/or cannulas specification are same as that for the bone washing technique described above.

FIGS. 1A and 1B show a photograph (FIG. 1A) and a matching radiograph (FIG. 1B) of a humeral head into which two needles (Vidacare, San Antonio, Tex.) or cannulas are inserted of the present invention in a model pig humeral head. The present invention allows the user to either inject and/or aspirate or both (i.e. positive and/or negative pressure washing), decreases the pressure of injection associated with single needle technique, and minimizes leakage. In the prior art using the single needle technique it is known that the leakage of bone promoting factors, such as BMP-2 leads to the formation of bone outside the femoral head as a result of leakage, which greatly increases the morbidity of the procedure. The present invention eliminates leakage and the growth of bone outside the femoral head. In particular, a material that is sufficiently viscous is injected/aspired that prohibits its release outside the femoral head, and/or plugs (e.g., biodegradable plugs) can be inserted into the openings to prevent leakage.

FIG. 2 shows a femoral head of a pig into which two needles or cannulas are inserted and are connected to syringes, the top syringe having a clear washing fluid, and the bottom syringe showing cell debris and fat in the washing fluid after traversing the femoral head. By washing out necrotic bone to remove necrotic cell debris and inflammatory factors the present invention improve bone healing.

Figure 3B:
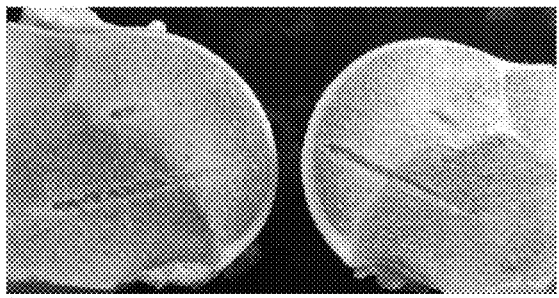
FIG. 3B shows a cross-section of an unwashed femoral head.
Figure 3C:
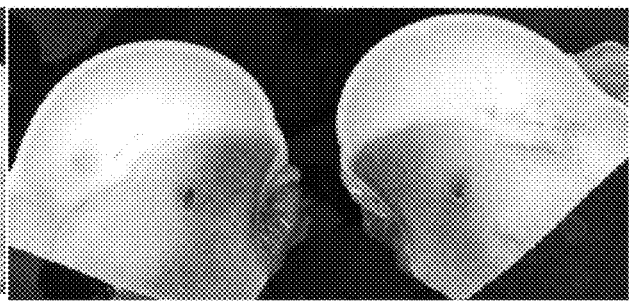
FIG. 3C shows a cross-section of a femoral head washed according to the present invention.
Figure 4:
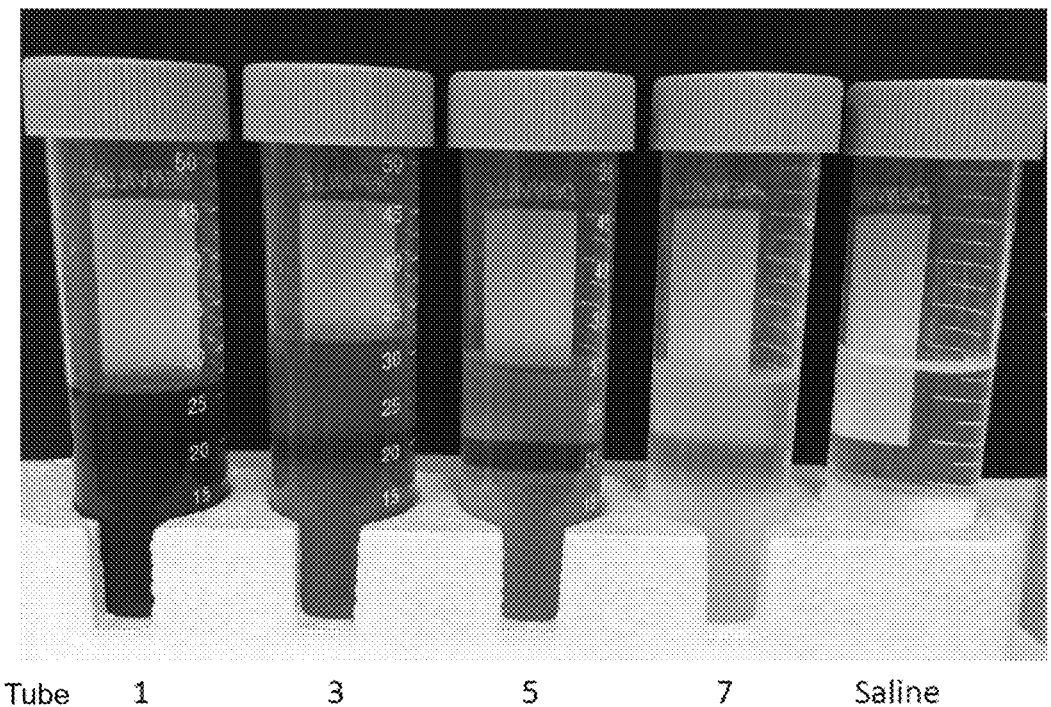
FIG. 4 shows a progression of washes of the femoral head shows in FIG. 3C and on the right the initial saline.

FIG. 3A shows on the left an unwashed femoral head of a pig, and the right a washed femoral head using the present invention. FIG. 3B shows a cross-section of an unwashed femoral head of a pig. FIG. 3C shows a cross-section of a femoral head of a pig washed according to the present invention. FIG. 4 shows a progression of washes of the femoral head of a pig shows in FIG. 3C and on the right the initial saline, which demonstrates the removal of dead cell debris, necrotic marrow fat, and/or inflammatory factors.

Figure 5A:
FIGS. 5A and 5B show a low and a high magnification, respectively, of the wash solution after cyto-spin to demonstrate that the solution contains cell debris from the femoral head.
Figure 5B:
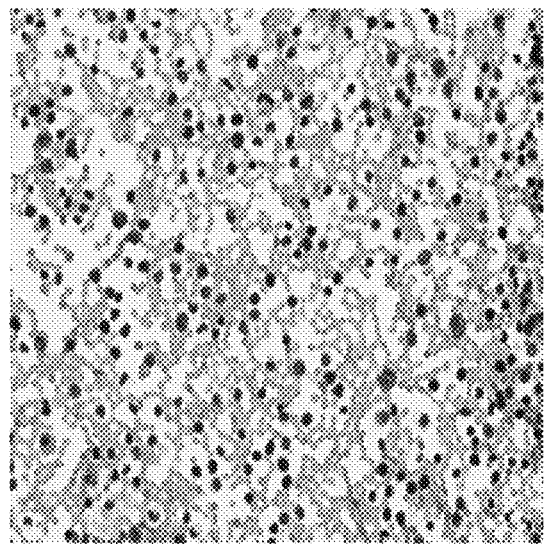

FIGS. 5A and 5B show a low and a high magnification, respectively, of the wash solution after cyto-spin to demonstrate that the solution contains cell debris from the femoral head of a pig. The wash solution was shown to contain cell debris that was washed out of the femoral head.

FIGS. 6A and 6B each show the histology at a low (4×) and a high (10×) magnification of the unwashed femoral head (FIG. 6A) and the washed femoral head (FIG. 6B) according to the present invention.

FIGS. 7A to 7C show the histology of the femoral head without (FIG. 7A), with a saline wash (FIG. 7B) and with an ethanol and saline wash (FIG. 7C) to remove fat and cell debris. It was found that saline wash removes fat and cell debris, while ethanol further removes fat. Both wash solutions were shown to create space for bone stimulating biomaterials including marrow stem cells.

Figure 8A:
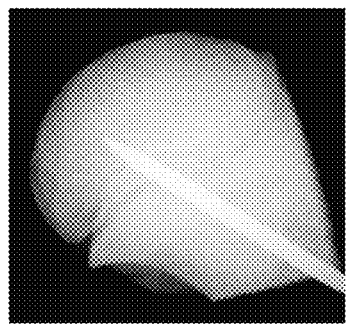
FIG. 8A shows a single needle of the prior art (left, radiograph), and the distribution of an imaging agent injected into the femoral head (right) through the single opening.
Figure 8A:
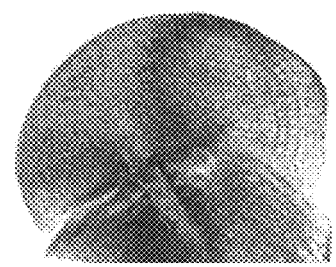
Figure 8B:
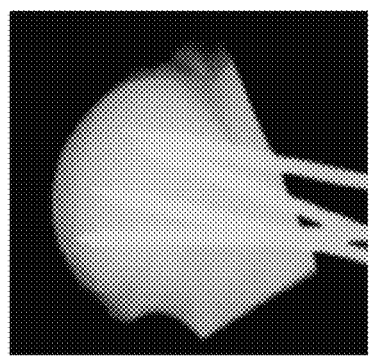
FIG. 8B shows a multiple needle (left, radiograph), wash, and injection of the distribution of an agent injected into the femoral head (right) using a four opening method in which one or two needles or cannulas are used to wash and two or three needles used to remove the wash and, likewise, the delivery the imaging agent using the present invention.
Figure 8B:

FIG. 8A shows a single needle of the prior art (left, radiograph), and the distribution of an imaging agent injected into the femoral head (right) through the single opening. FIG. 8B shows a multiple needle (left, radiograph), wash, and injection of the distribution of an agent injected into the femoral head (right) using a four opening method in which one or two needles or cannulas are used to wash and two or three needles used to remove the wash and, likewise, the delivery the imaging agent using the present invention. The images on the right clearly show that the multiple needle/cannula method provides a much wider distribution of the visualization agent, while the single injection shows an umbrella-like distribution.

Figure 9:
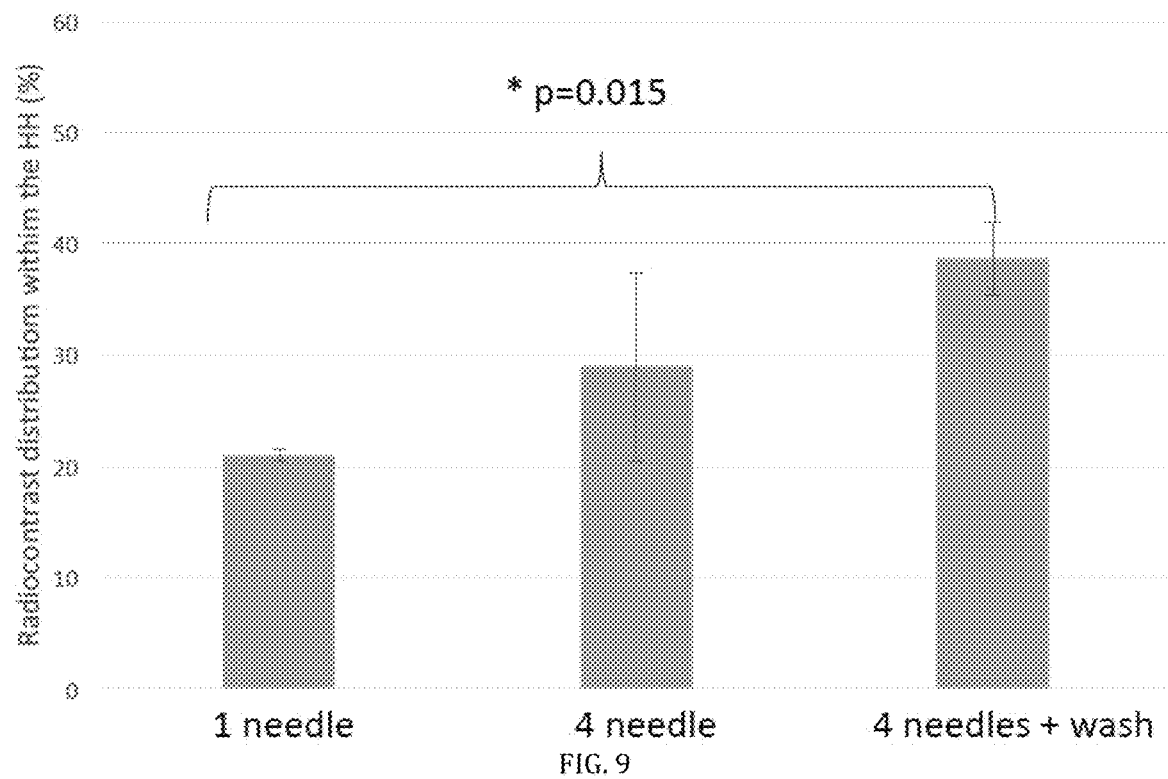
FIG. 9 is a graph that compares the prior art with a 4 needle/cannula method, and the 4 needle/cannula method that also included the wash, and the distribution of the imaging agent in the femoral head.

FIG. 9 is a graph that compares the prior art with a 4 needle/cannula method, and the 4 needle/cannula method that also included the wash, and the distribution of the imaging agent in the femoral head.

Figures 10A, 10B, 10C:
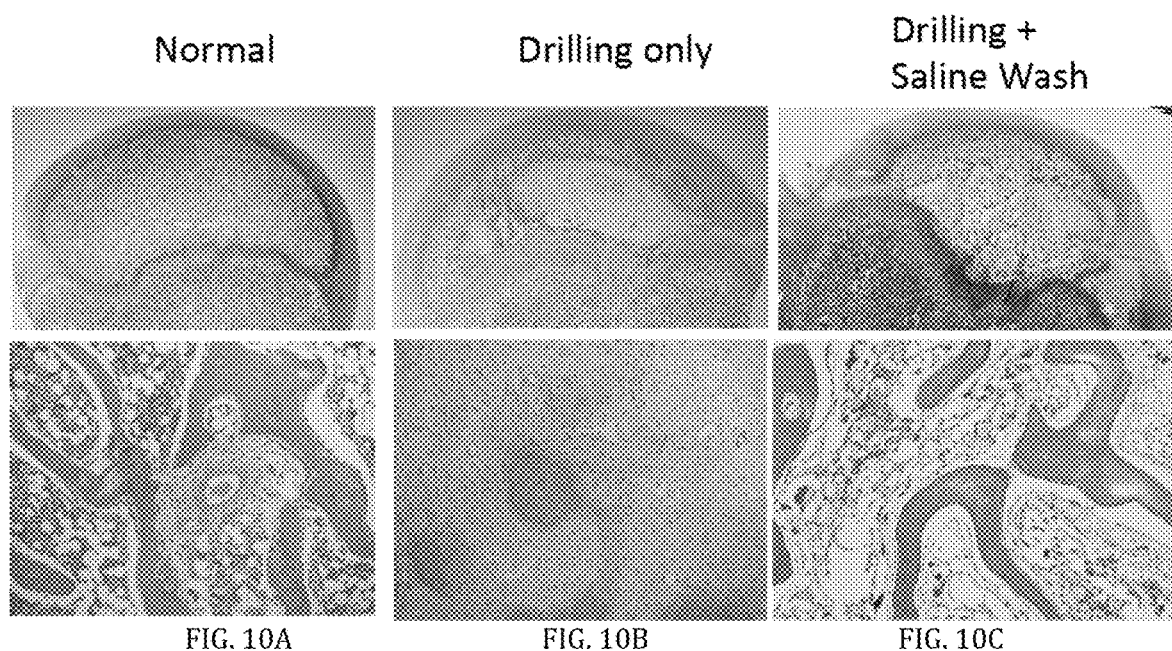
FIGS. 10A to 10C shows the histology of the femoral head of a normal femoral head (FIG. 10A), after multiple drilling only (FIG. 10B) and multiple drilling and saline wash (FIG. 10C), wherein bone washing improved bone healing, showed decreases resorption and increased bone formation.

FIGS. 10A to 10C show the histology of the femoral head of a normal femoral head (FIG. 10A), after drilling only (FIG. 10B) and drilling and saline wash (FIG. 10C), wherein bone washing improved bone healing, showed decreases resorption and increased bone formation. Thus, the bone washing of the present invention improves bone healing, shows decreased resorption, and increased bone formation.

Figure 11A:
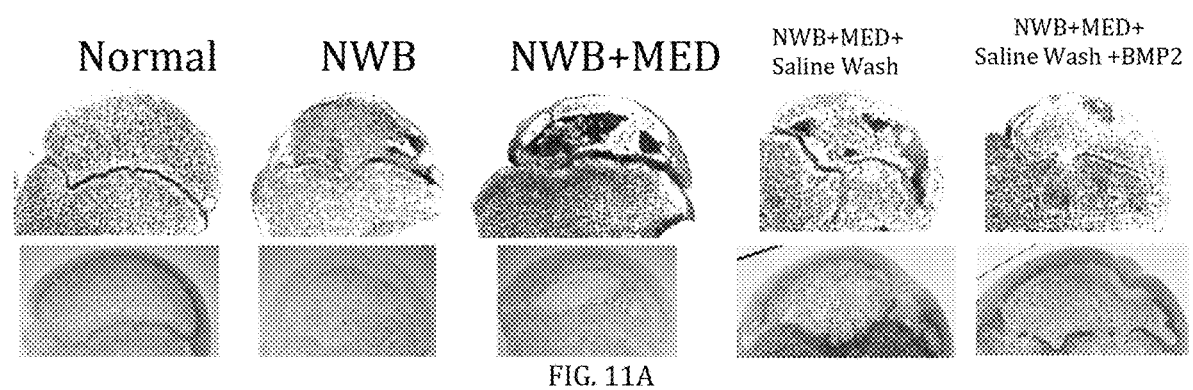
FIG. 11A shows micro-computer tomography (Micro-CT) and histologic assessments comparing a normal femoral head, a femoral head treated with the non-weight bearing method of the prior art, the non-weight bearing and multiple drilling of the prior art, non-weight bearing+multiple drilling+saline wash of the present invention, and non-weight bearing+multiple drilling+saline wash+BMP2/gelatin injection of the present invention.
Figure 11B:
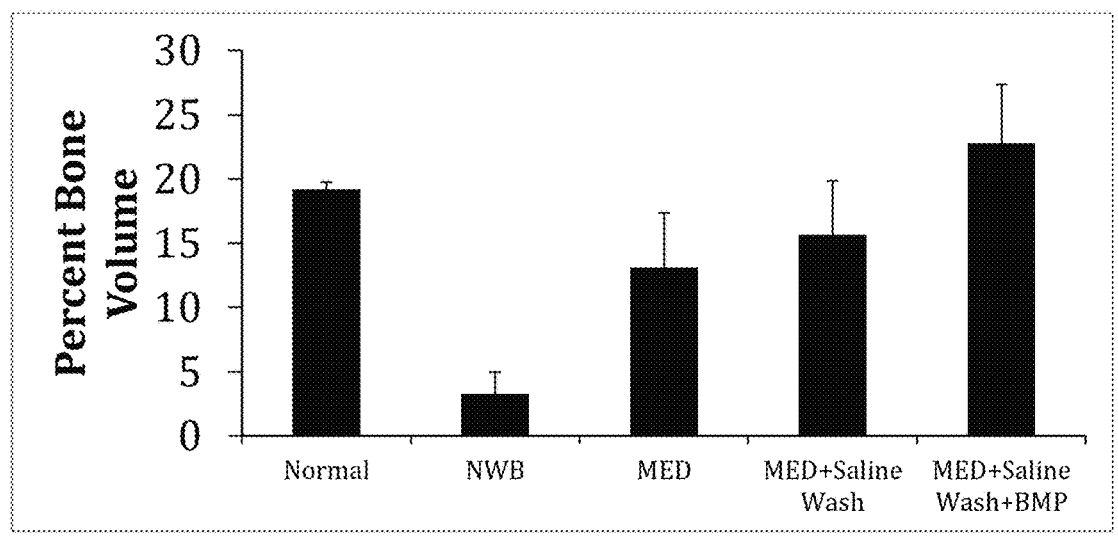
FIG. 11B is a graph that compares a percent bone volume of a normal femoral head, a femoral head treated with the non-weight bearing method of the prior art, the non-weight bearing and multiple drilling of the prior art, non-weight bearing+multiple drilling+saline wash of the present invention, and non-weight bearing+multiple drilling+saline wash+BMP2/gelatin injection of the present invention.

FIG. 11A shows a micro-computer tomography (Micro-CT) assessment compares a normal femoral head, a femoral head treated with the non-weight bearing method of the prior art, the non-weight bearing and multiple drilling of the prior art, and non-weight bearing+drilling,+saline wash of the present invention. FIG. 11B is a graph that compares a percent bone volume of a normal femoral head, a femoral head treated with the non-weight bearing method of the prior art, the non-weight bearing and multiple drilling of the prior art, and non-weight bearing+multiple drilling,+saline wash of the present invention.

Figure 12:
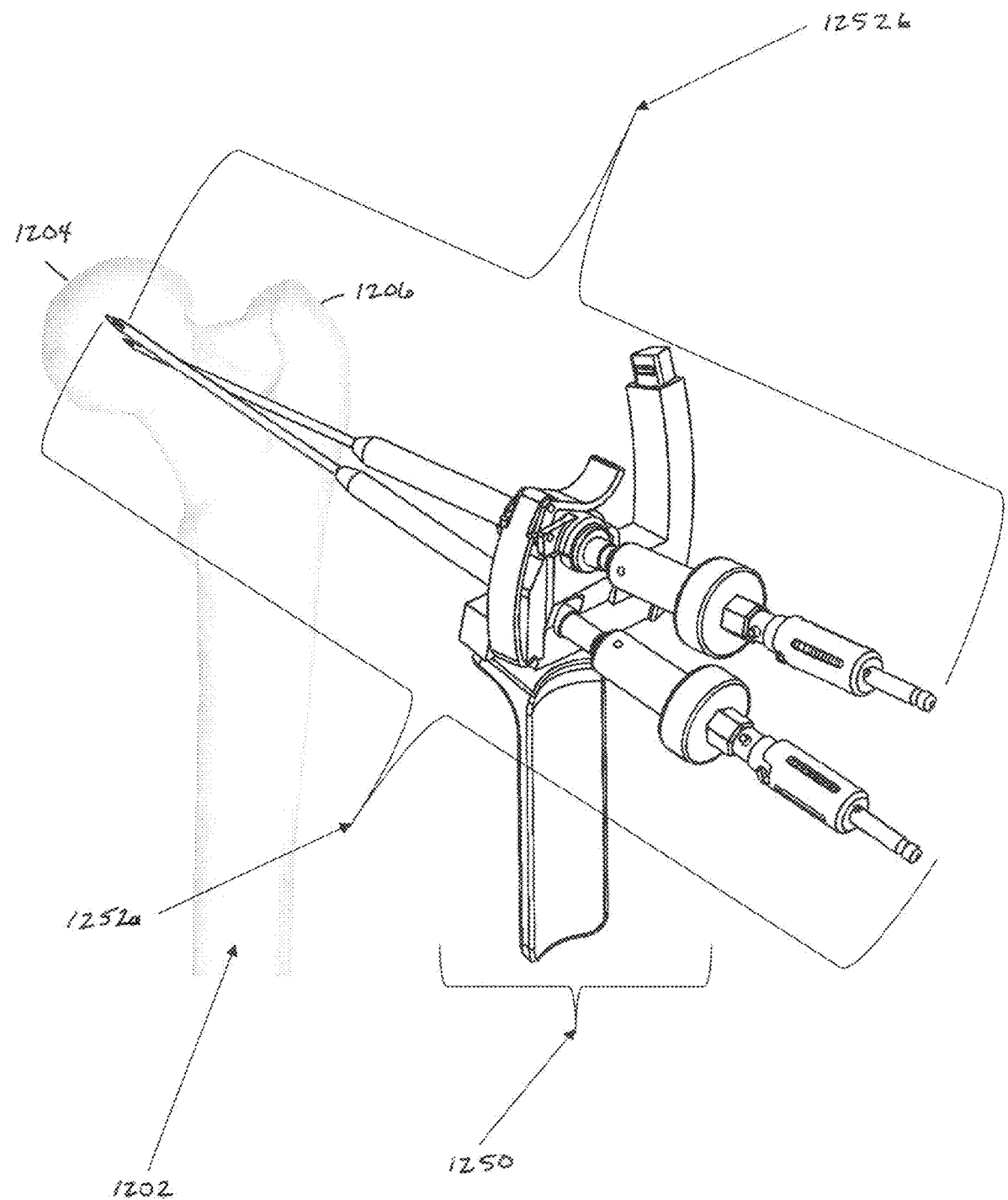
FIG. 12 illustrates the upper end of a human femur with an embodiment of a needle targeting device according to the present invention.

FIG. 12 shows the upper end of a human femur 1202, including the femoral head 1204 and the greater trochanter

1206. FIG. 12 also illustrates an embodiment of the present invention, the needle targeting guide 1250 with the first and second needle assemblies, 1252*a* and 1252*b*, respectively. The needle targeting guide 1250 is shown in place directing the needle assemblies 1252*a* and 1252*b* toward the human femoral head 1204.

Figure 13:
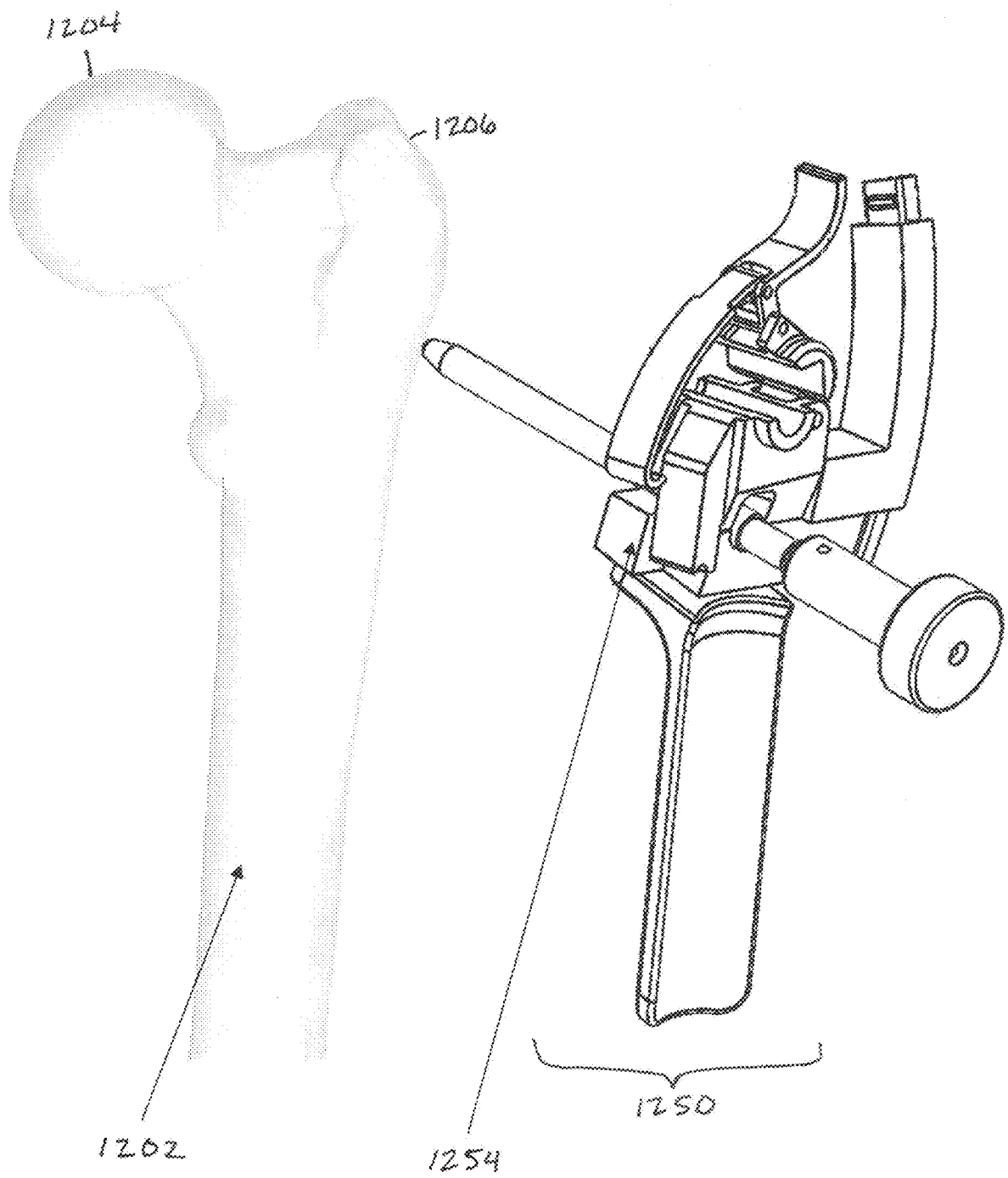
FIG. 13 shows a first step in placing the needle targeting device relative to a human femur according to the present invention.

FIG. 13 shows a first step in placing the needle targeting guide 1250 relative to the human femur 1202 according to the present invention. FIG. 13 shows the human femur 1202, the femoral head 1204, and the greater trochanter 1206. FIG. 13 also depicts the needle targeting guide 1250 and the central stationary assembly 1254. FIG. 13 illustrates the central stationary assembly 1254 placed along the axis of the greater trochanter 1206 and driven up to the lateral surface of the human femur 1202.

Figure 14:
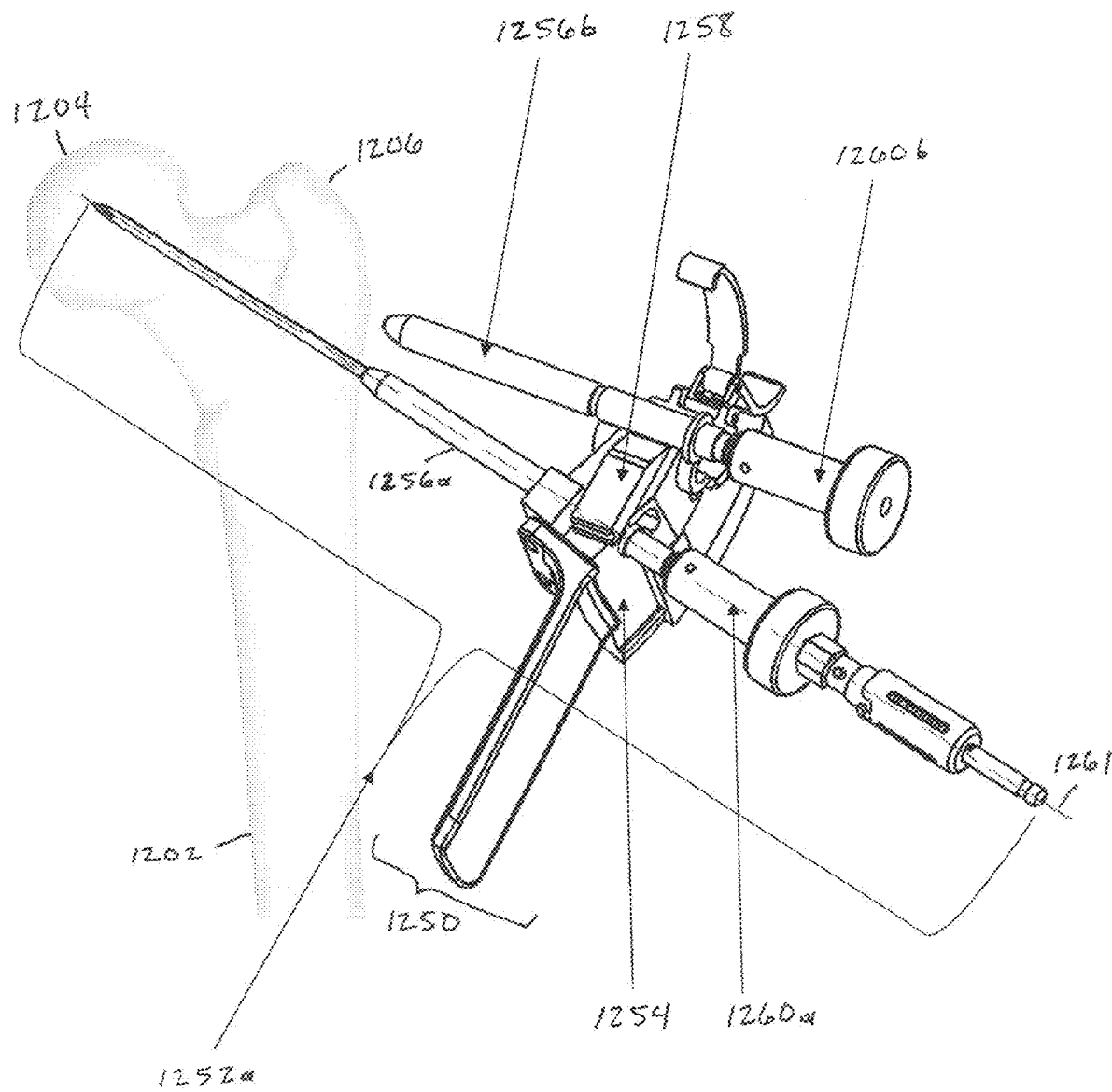
FIG. 14 shows the upper end of a human femur with the needle targeting device according to the present invention, with one needle assembly in place.

FIG. 14 depicts the human femur 1202, the femoral head 1204, and the greater trochanter 1206. FIG. 14 also shows the needle targeting guide 1250, the first needle assembly 1252*a*, the central stationary assembly 1254, guide cannulas 1256*a* and 1256*b*, adjustable subassembly 1258, and the first and second depth adjustments 1260*a* and 1260*b*. FIG. 14 shows the placement of the first needle assembly 1252*a* through the central portion of the central stationary assembly 1254. Once the central stationary assembly 1254 is placed, the entire needle targeting guide 1252 can pivot about its longitudinal axis 1261. The guide cannula 1256*b* is placed (roughly) at the desired trajectory for the second needle assembly 1252*b* (not shown). The needle targeting guide 1250 can then be pivoted to a location to engage the guide cannula 1256*b*. The first and second depth adjustments, 1260*a* and 1260*b*, respectively, are attached using threaded interfaces to the central stationary assembly 1254 and the adjustable subassembly 1258, respectively, and the guide cannulas 1256*a* and 1256*b* respectively, and can be used as hard stops for the needle assemblies 1252*a* and 1252*b* so that the drilling depth can be adjusted to the desired location intraoperatively.

Figure 15:
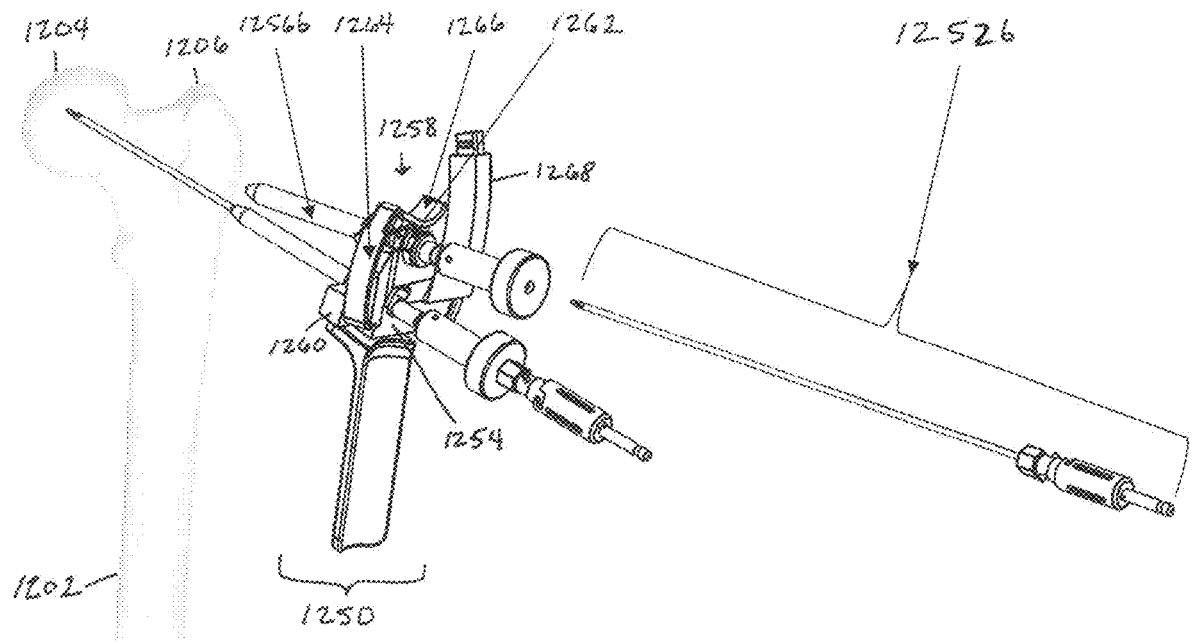
FIG. 15 the upper end of a human femur with the needle targeting device according to the present invention, with one needle assembly in place and a second needle assembly ready for insertion.

FIG. 15 shows the guide cannula 1256*b* latched into the needle targeting guide 1250 by placing the guide clamp 1262 over the guide cannula 1256*b*, engaging the tension clamp 1264 and actuating the tension clamp lever 1266 to place the tension clamp 1264 into tension. By latching the guide cannula 1256*b* to the needle targeting guide 1250, the trajectory and depth of the second needle assembly 1252*b* can be set. The adjustable subassembly 1258 can be moved relative to the central stationary assembly 1254 using a protractor slide interface 1268 that brings the two components together. Movement of the adjustable subassembly 1258 relative to the central stationary assembly 1254 through the protractor arc can cause the tip locations of the needle assemblies 1252*a* and 1252*b* to converge or diverge as desired.

Figure 16:
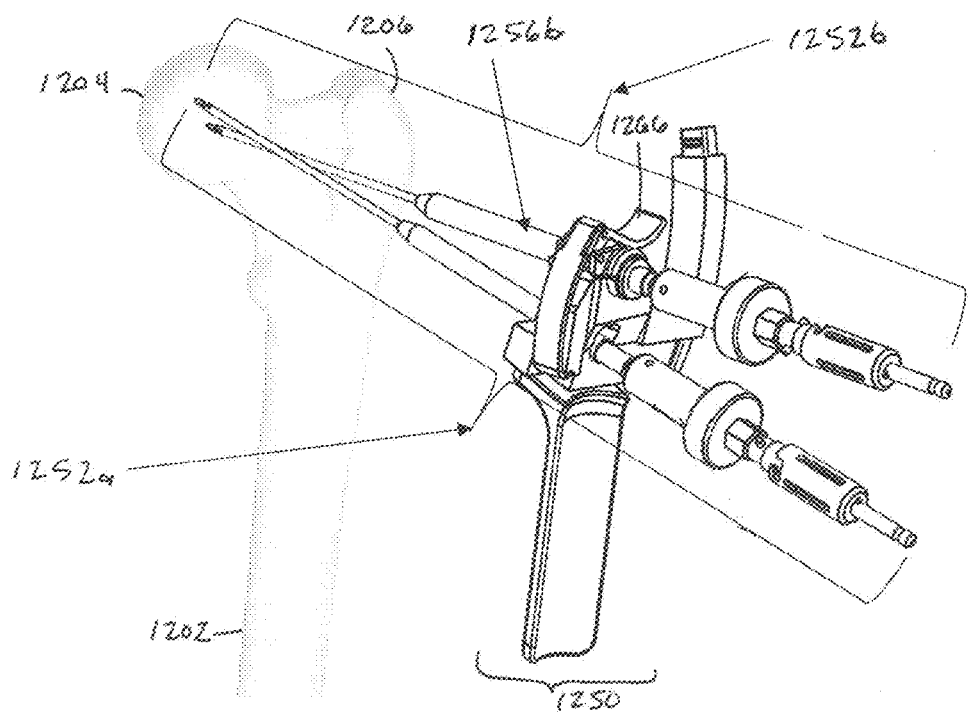
FIG. 16 shows the upper end of a human femur with the needle targeting device according to the present invention, with two needle assemblies in place.

FIG. 16 shows the placement of the second needle assembly 1252*b*. After this has been done, the guide cannula 1256*b* and the second needle assembly 1252*b* can be disengaged from the needle targeting guide 1250 by reverse actuating the tension clamp lever 1266 and pivoting the needle targeting device about the first needle assembly 1252*a*. In this fashion, multiple guide cannulas and needle assemblies may be placed within the human femur 1202.

Figure 17:
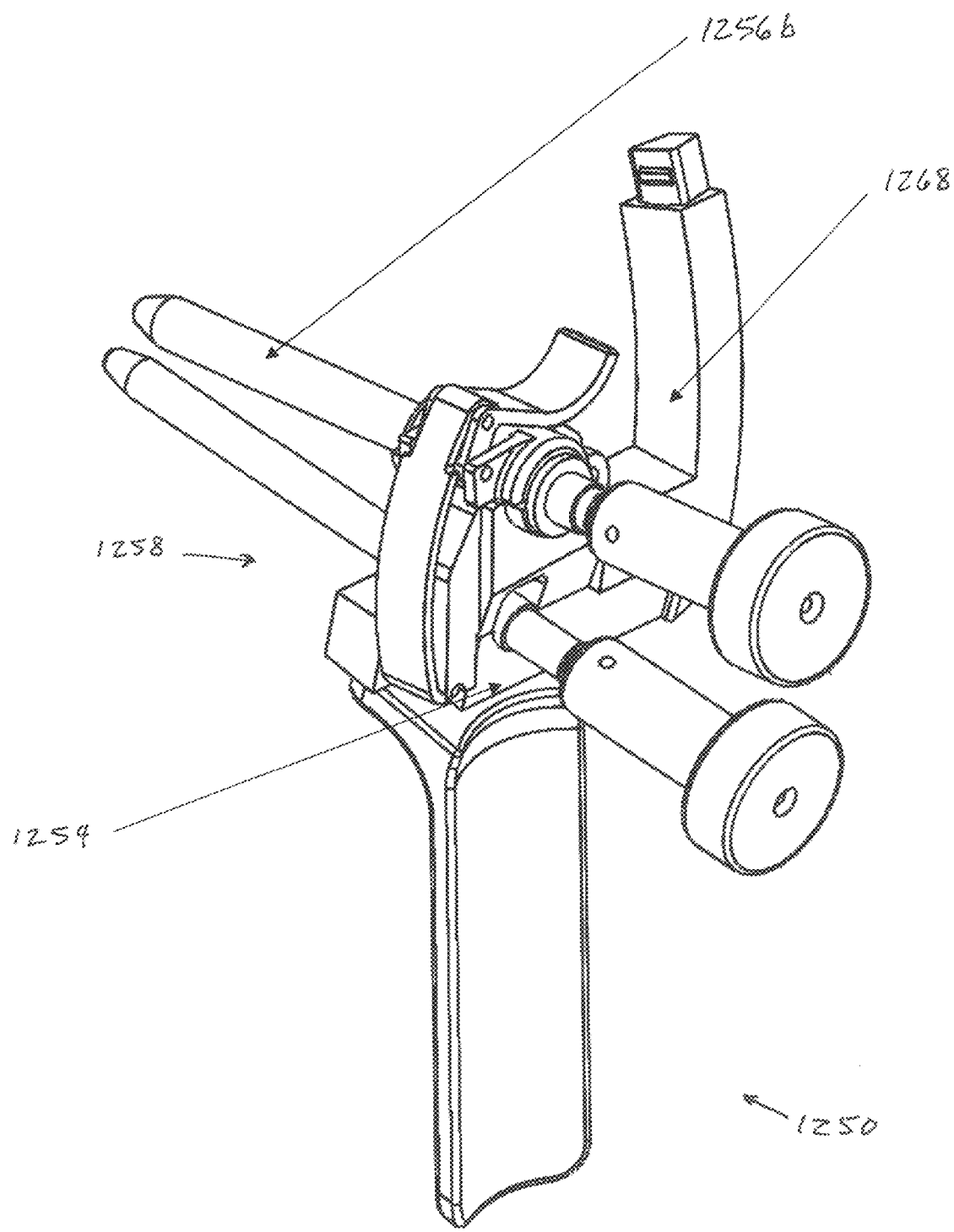
FIG. 17 shows a central stationary assembly with an adjustable subassembly of the needle targeting device according to the present invention.

FIG. 17 shows a needle targeting guide 1250 which shows the engagement of the central stationary assembly 1254 with the adjustable subassembly 1258 using the protractor slide interface 1268. A guide cannula 1256*b* is shown latched into place.

Figure 18:
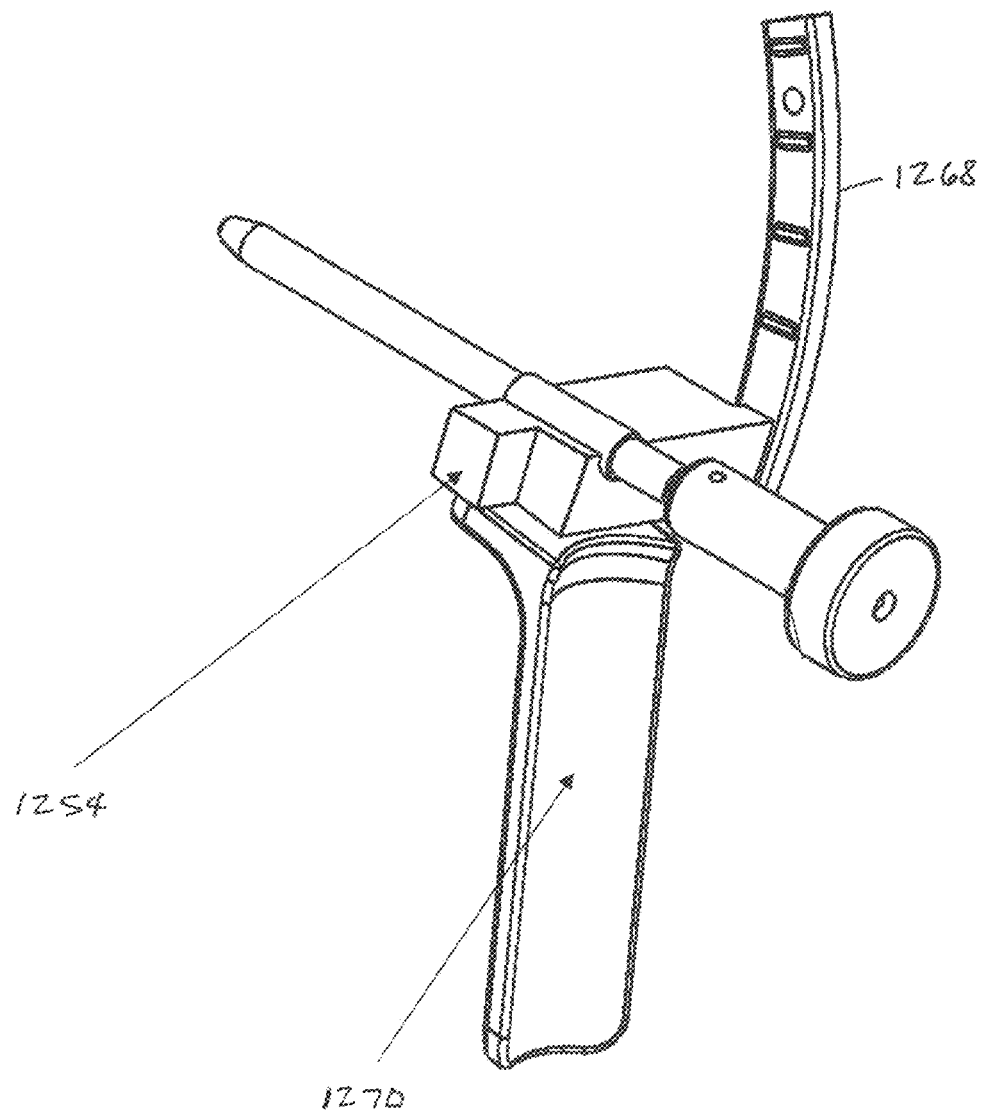
FIG. 18 depicts a central stationary assembly of the needle targeting device according to the present invention.

FIG. 18 shows a central stationary assembly 1254 with the adjustable subassembly 1258 (not shown) disengaged. This detail shows the handle 1270 in place which facilitates usage intraoperatively. The male protractor arm component of the protractor slide interface 1268 is visible at top right.

Figure 19:
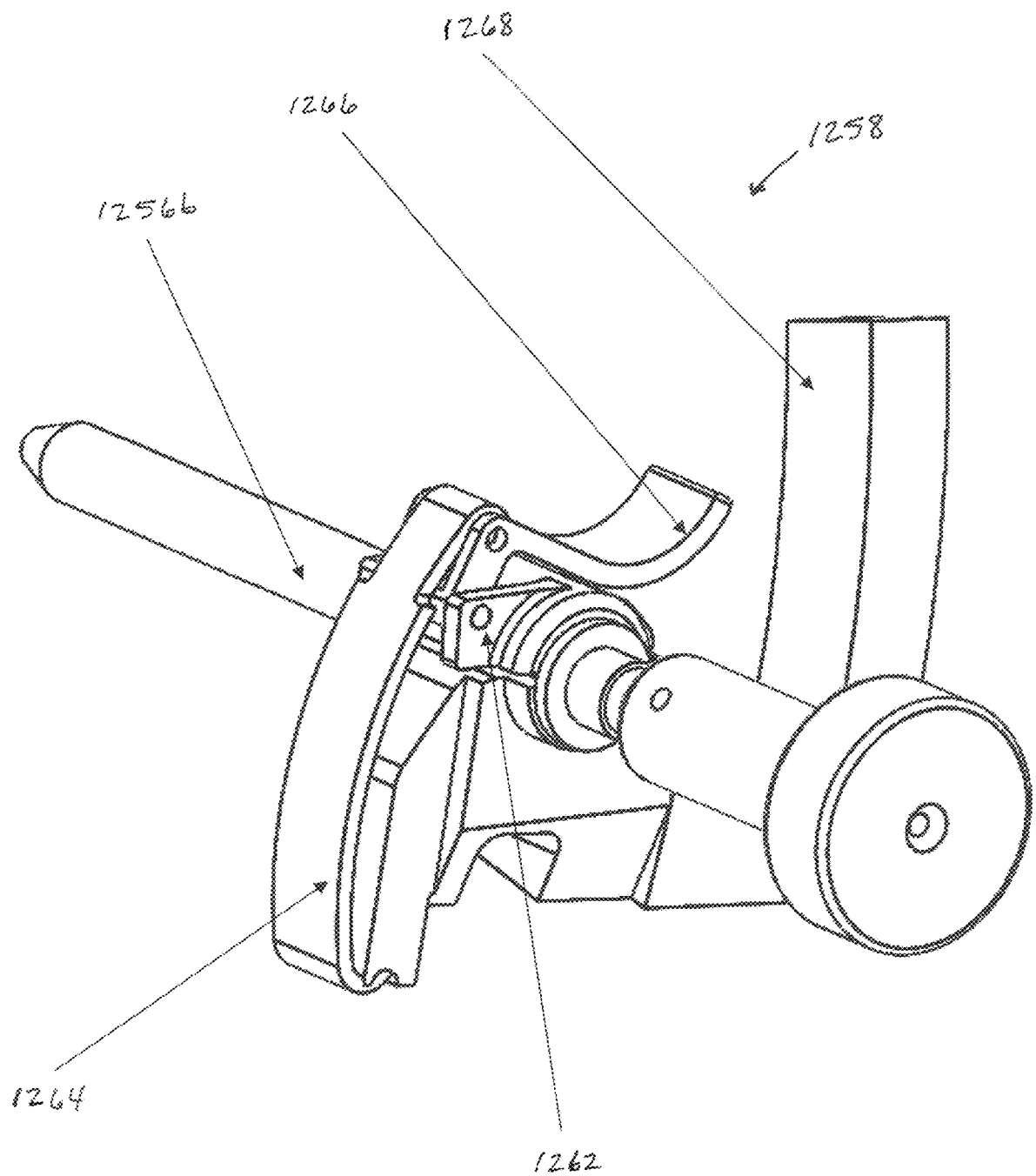
FIG. 19 depicts an adjustable subassembly of the needle targeting device according to the present invention.

FIG. 19 shows the adjustable subassembly 1258 with the guide cannula 1256*b* engaged using a clamping mechanism including the guide clamp 1262, the tension clamp 1264, and the tension clamp lever 1266 to positively secure the guide cannula 1256*b* to the adjustable subassembly 1258. Securing the guide cannula 1256*b* in this manner sets the trajectory for second needle assembly 1252*b* placement. The female protractor arm component of the protractor slide interface 1268 is shown.

Figure 20:
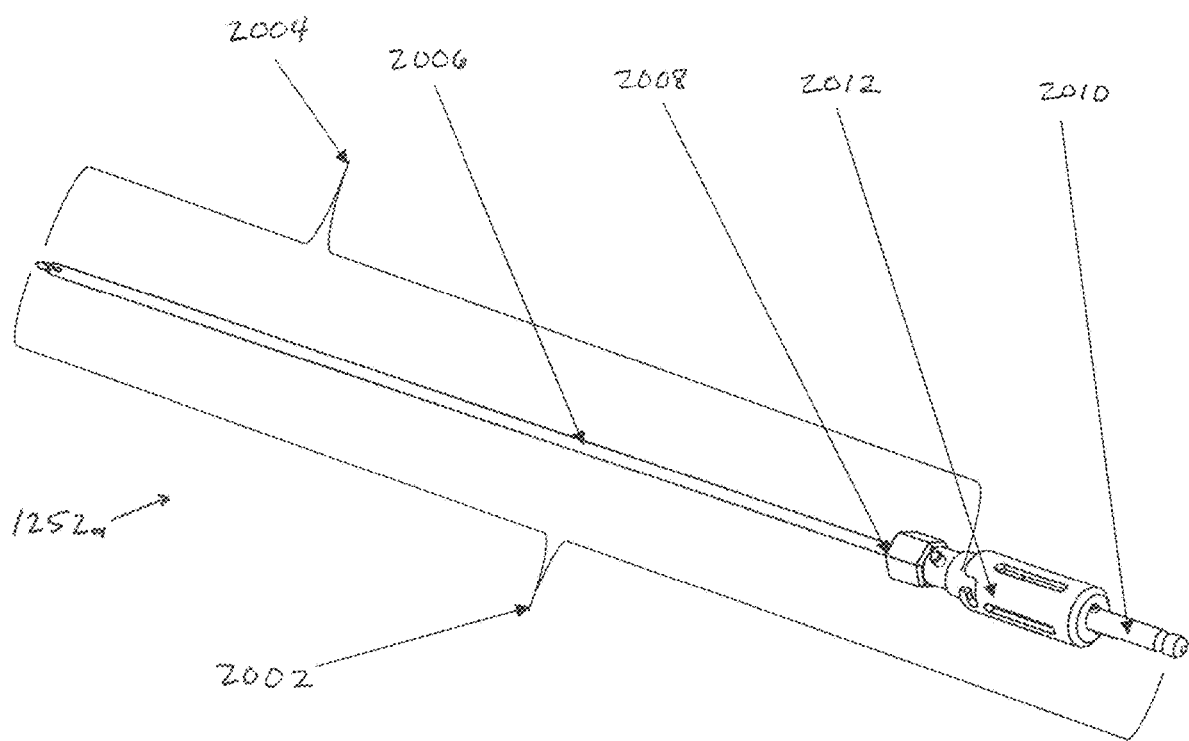
FIG. 20 illustrates a needle assembly according to the present invention.

FIG. 20 shows the first needle assembly 1252*a*. The second needle assembly 1252*b* is similar to the first needle assembly 1252*a*, so this description generally applies to both items. The removable drilling assembly 2002 (also known as the trocar assembly 2002) inserts through the needle cannula assembly 2004 (including the needle cannula 2006) and rotationally engages together via a locking mechanism including a male-female interconnection between the luer lock 2008 and the drill interface 2010. The drilling assembly 2002 can be locked together with the needle cannula assembly 2004 along their lengths using a locking mechanism including the lock collar 2012 and the luer lock 2008. The lock collar 2012 can be pushed downwards and engaged onto the posts of the luer lock 2008.

Figure 21:
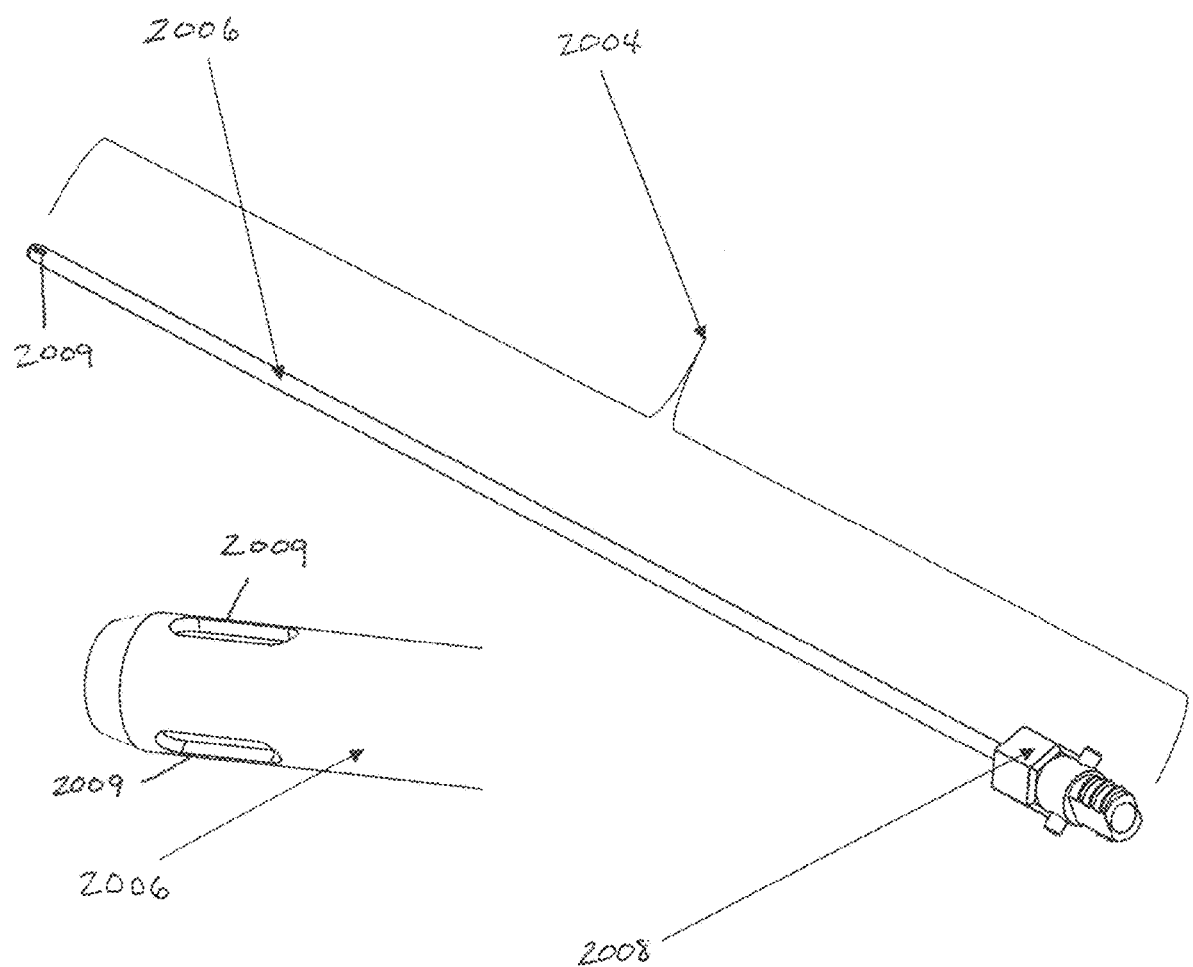
FIG. 21 depicts needle cannula assembly according to the present invention.

FIG. 21 shows the needle cannula assembly 2004. The needle cannula 2006 is attached to the luer lock 2008 and this connection provides a fluid tight connection for drug delivery into the bone once the drilling assembly 2002 has been removed. There are fenestrations 2009 on the distal end of the needle cannula 2006 in order to facilitate dispersal of drugs within the bone.

Figure 22:
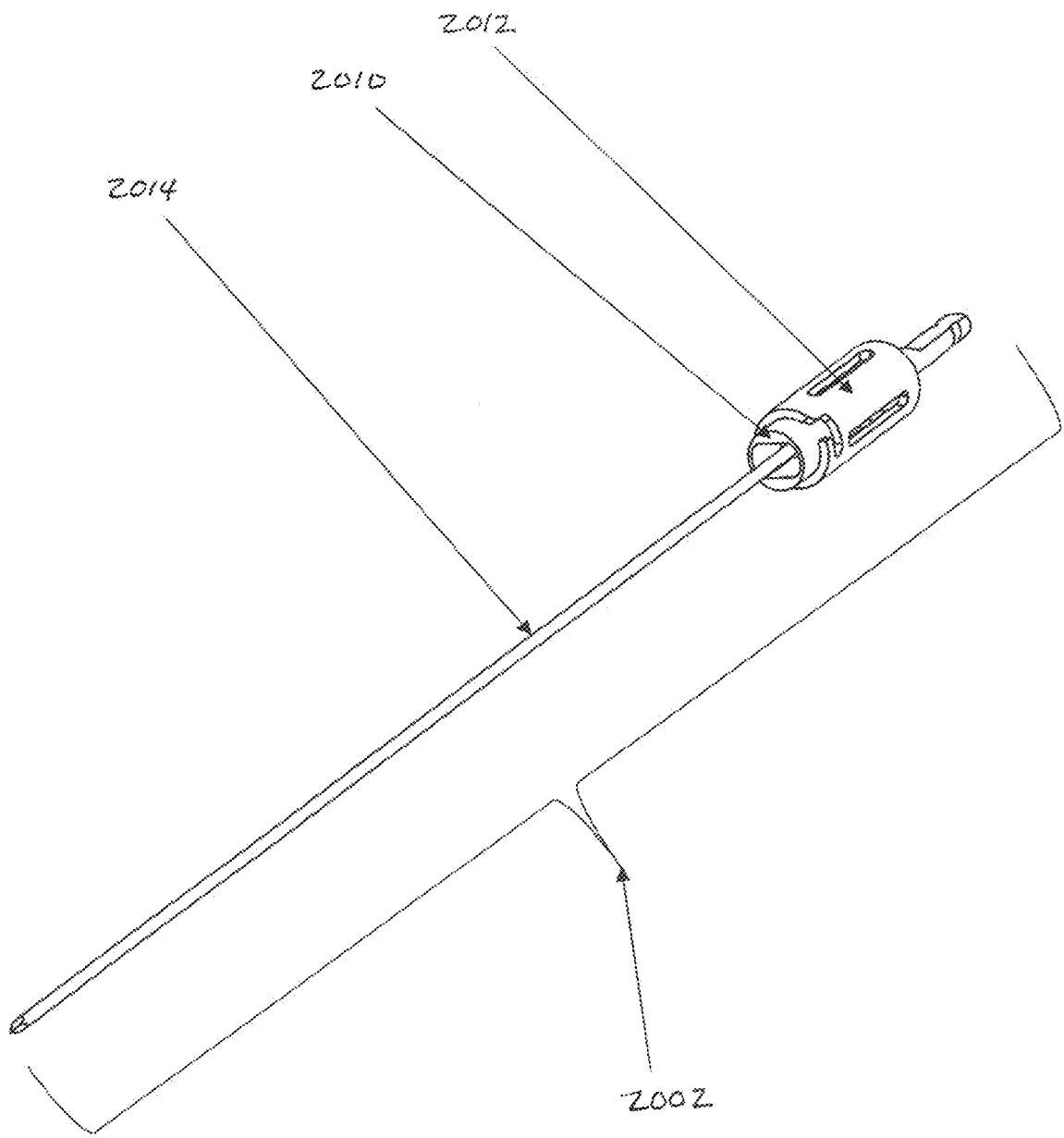
FIG. 22 shows a drilling assembly according to the present invention.

FIG. 22 shows the drilling assembly 2002. The drilling wire 2014 is securely attached to the drill interface 2010. The female pocket of the drill interface 2010 is shown. The flats (not shown) within the pocket of the drill interface 2010 engage with the flats on the luer lock 2008 to provide rotational fixation when they are engaged. The lock collar 2012 engages with the posts of the luer lock 2008 to lock the drilling assembly 2002 to the needle cannula assembly 2004 (not shown) along their lengths.

Figure 23:
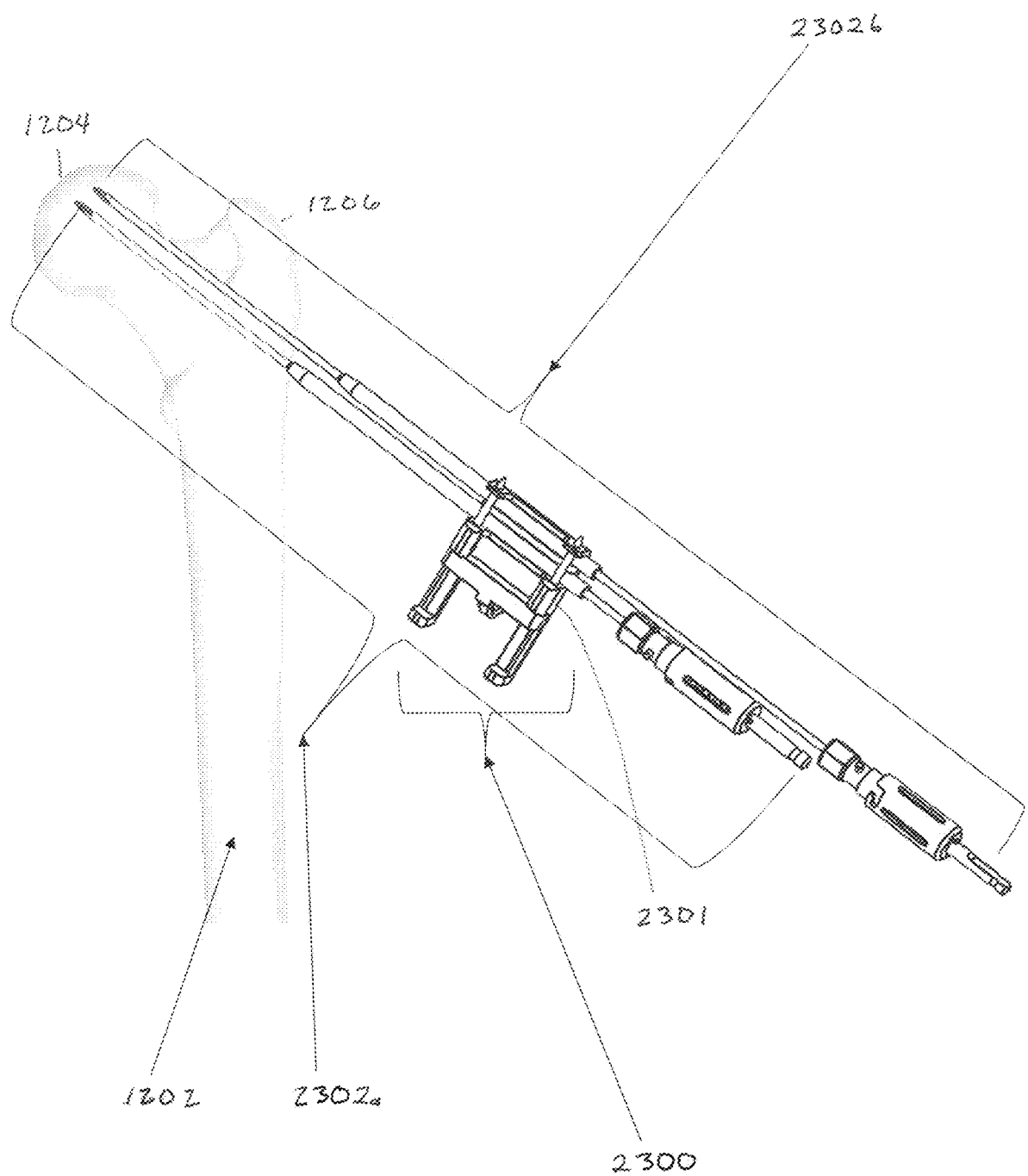
FIG. 23 shows the upper end of a human femur with another embodiment of a needle targeting device according to the present invention.

FIG. 23 shows the upper end of a human femur 1202 with another embodiment of the present invention. The human femur 1202 includes the femoral head 1204 and the greater trochanter 1206. FIG. 23 also shows needle targeting guide 2300, including needle targeting guide frame 2301, directing first and second needle assemblies 2302*a* and 2302*b* toward the femoral head 1204.

Figure 24:
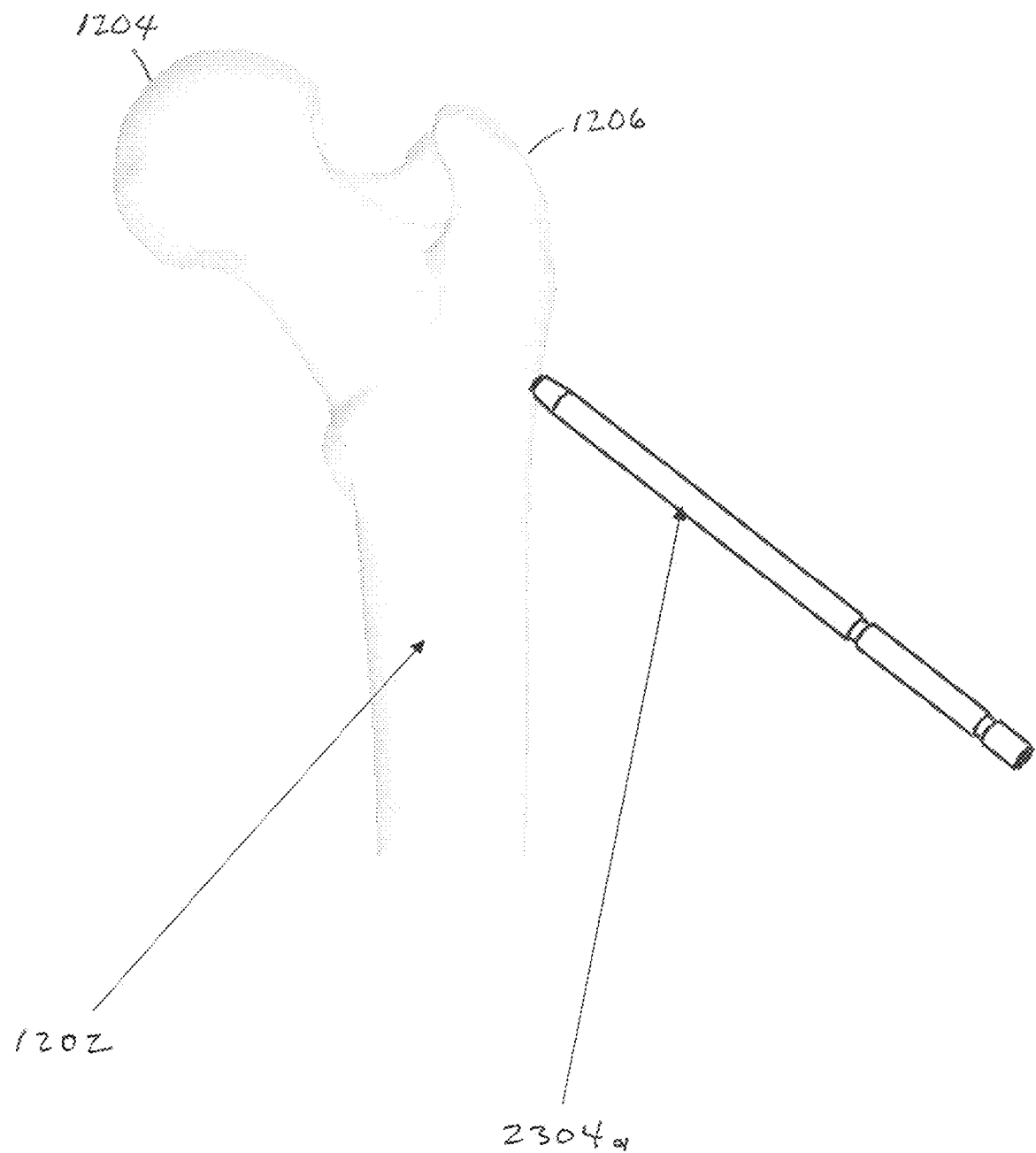
FIG. 24 shows a first step in placing the needle targeting device relative to a human femur according to the present invention.

FIG. 24 illustrates placing the needle targeting guide 2300 relative to the human femur 1202. FIG. 24 shows the human femur 1202, the femoral head 1204, and the greater trochanter 1206. Here, the guide cannula 2304*a* is placed along the axis of the greater trochanter 1206 and driven up to the lateral surface of the human femur 1202.

Figure 25:
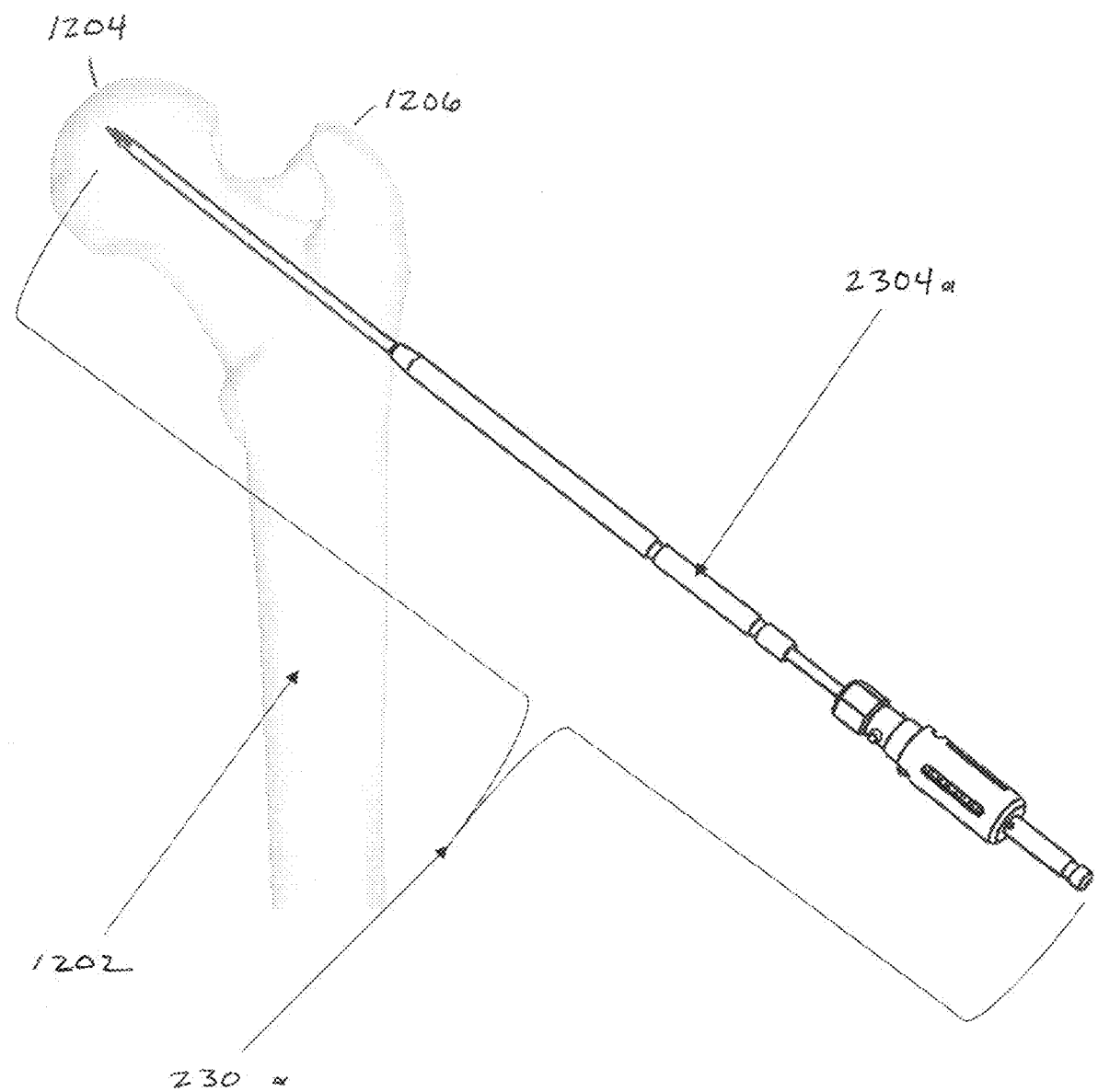
FIG. 25 depicts shows the upper end of a human femur with the needle targeting device according to the present invention, with one needle assembly in place.

FIG. 25 depicts the human femur 1202, the femoral head 1204, and the greater trochanter 1206. FIG. 25 also shows placement of first needle assembly 2302*a* through the guide cannula 2304*a*. The placement of the first needle assembly 2302*a* into the center of the human femur 1202 provides a stable axis of rotation whereby additional needles can be placed radially around this central location.

Figure 26:
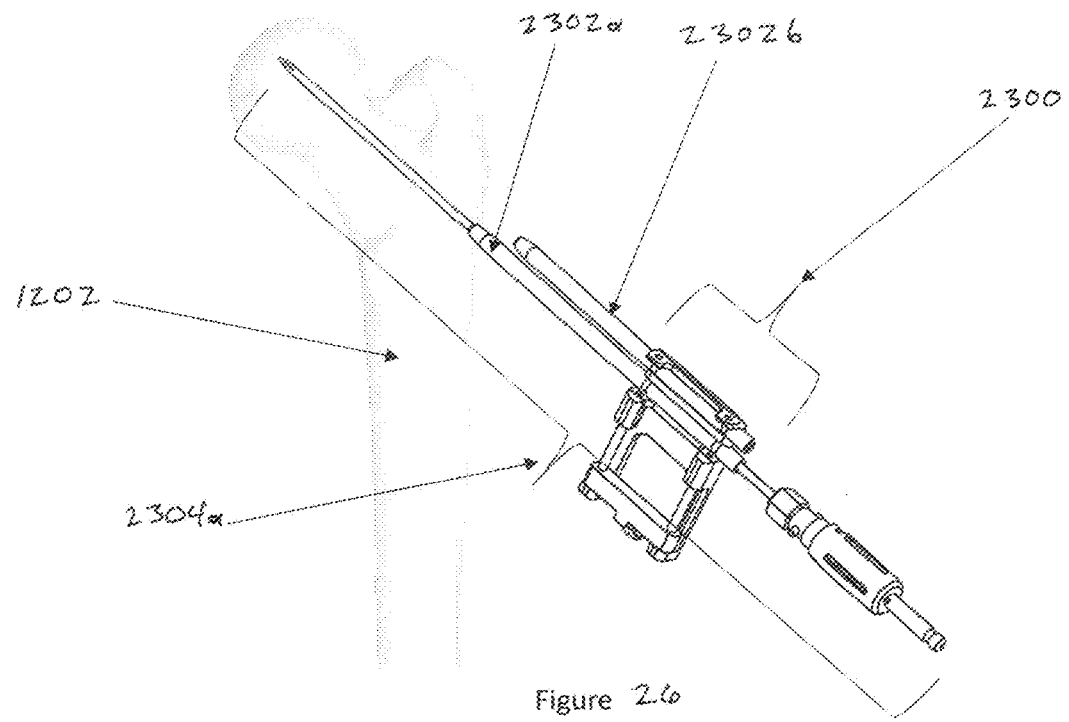
FIG. 26 illustrates the upper end of a human femur with the needle targeting device according to the present invention, with one needle assembly in place and a second guide cannula in place.

FIG. 26 illustrates needle targeting guide 2300 placed onto the guide cannula 2304*a*, which permits guide cannula 2304*b* to be roughly placed radially relative to the first needle assembly 2302*a*. The needle targeting guide 2300 uses a predefined distance between the axis of the guide cannula 2304a and the guide cannula 2304b. Multiple predefined distances may be provided in order to accommodate surgeon preferences and unique anatomical requirements.

Figure 27:
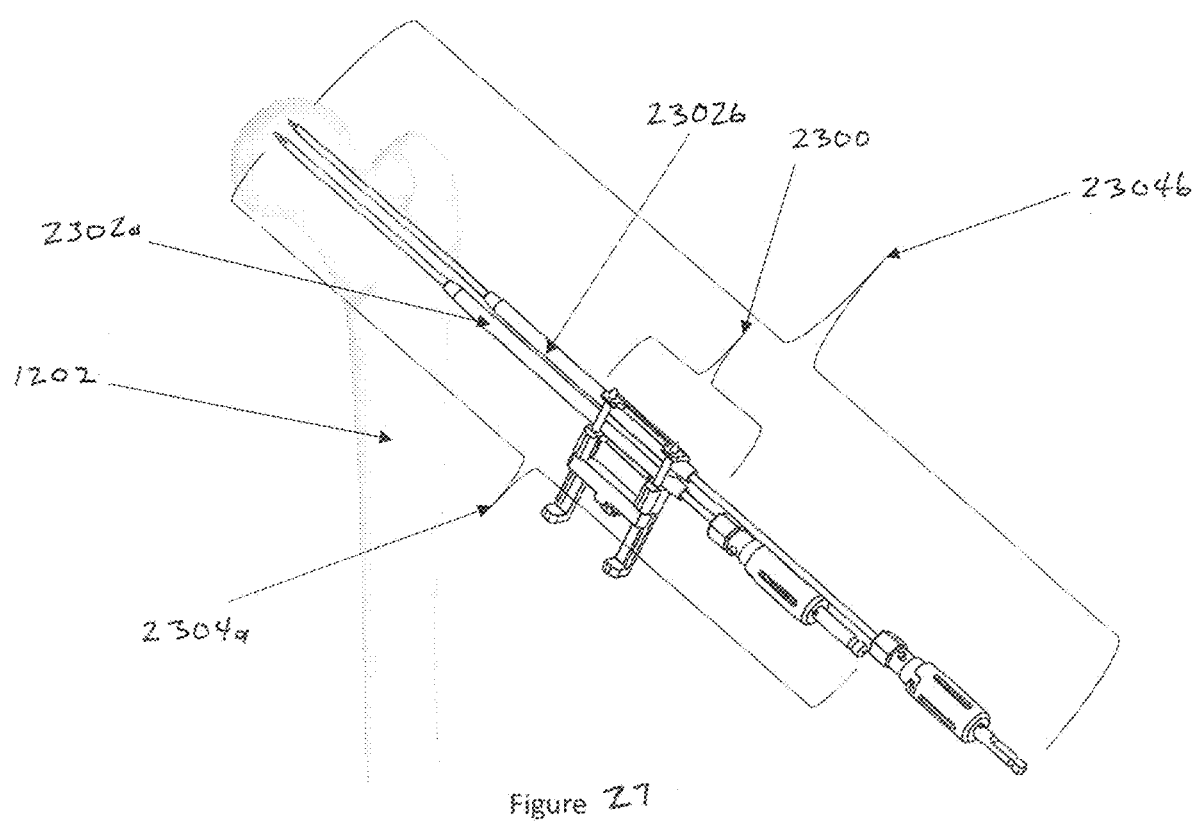
FIG. 27 shows the upper end of a human femur with the needle targeting device according to the present invention, with two needle assemblies in place.

FIG. 27 shows the needle targeting guide 2300 after being secured in place onto both the guide cannula 2304a and the guide cannula 2304b. By locking the needle targeting guide 2300 to guide cannulas 2304a and 2304b, the axes of the guide cannulas 2304a and 2304b parallel to one another for accurate targeting within the human femur 1202. Here, the second needle assembly 2302b is shown introduced into the femoral head 1204.

Figure 28:
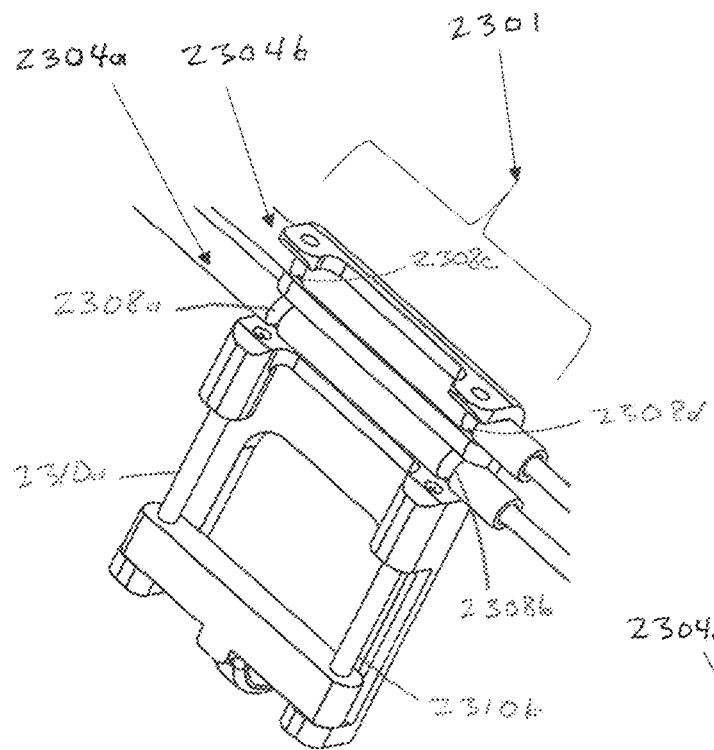
FIG. 28 depicts the needle targeting device including two guide cannulas in an unlocked state.
Figure 29:
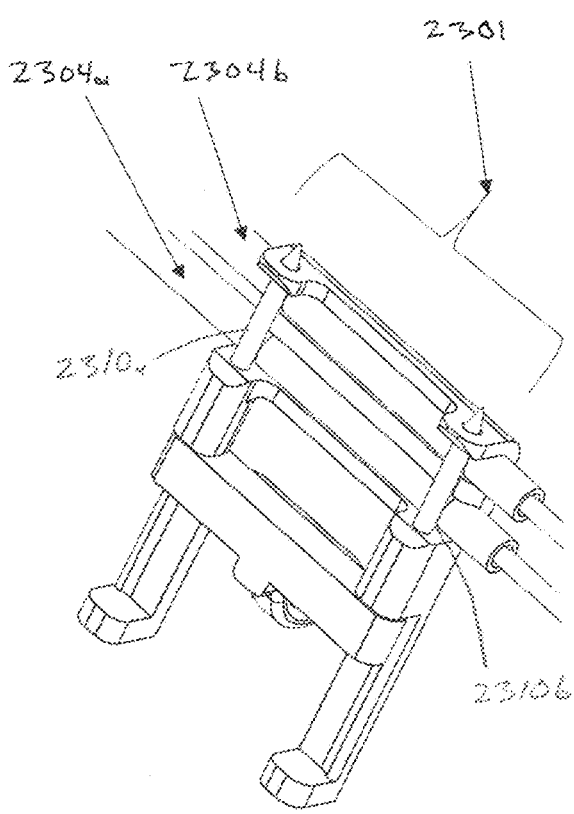
FIG. 29 depicts the needle targeting device including two guide cannulas in a locked state.

FIGS. 28 and 29 illustrate details of the needle targeting guide 2300. In FIG. 28, the needle targeting guide frame 2301 of the needle targeting guide 2300 has been placed around the guide cannulas 2304a and 2304b. There are grooves 2308a and 2308b circumferentially cut into the guide cannula 2304a and grooves 2308c and 2308d cut circumferentially into guide cannula 2304b. The locking pins 2310a and 2310b are shown retracted within needle targeting guide frame 2301. In FIG. 29, the locking pins 2310a and 2310b have been moved into place within the needle targeting guide frame 2301 where they engage the round grooves 2308a, 2308b, 2308c, and 2308d, thereby locking the guide cannulas 2404a and 2304b into place and orientation. One skilled in the art will recognize that there may be one groove 2038 cut into the guide cannulas 2304a and 2304b, or more than two, and one or more than two locking pins 2310; two grooves 2308 for each guide cannula 2304 and two locking pins 2310 are shown here as an example.

Figure 30:
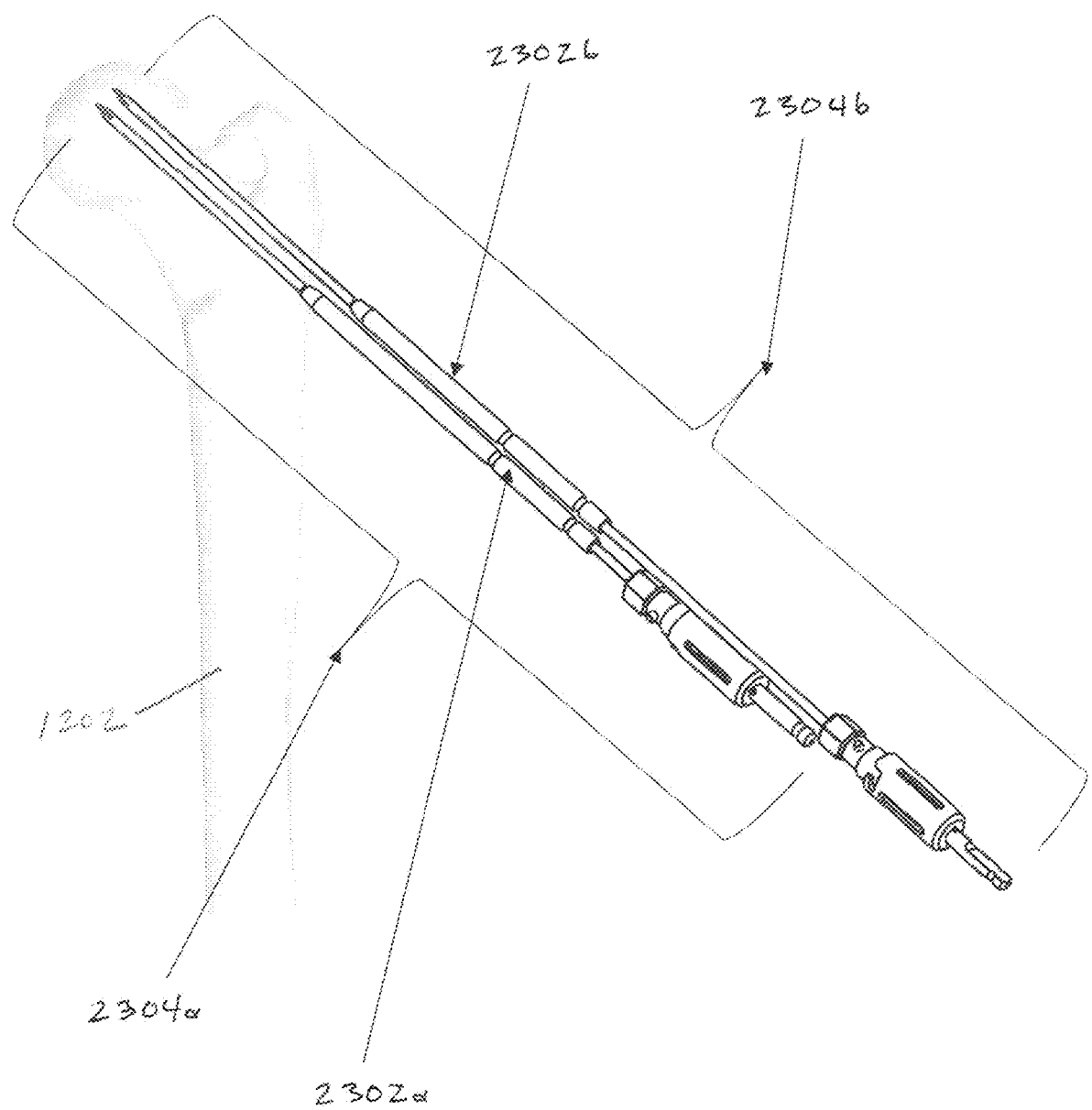
FIG. 30 shows the upper end of a human femur with two needle assemblies in place in the femur, after remove of the needle targeting guide frame.

FIG. 30 shows the guide cannulas 2304a and 2304b in place after the needle targeting guide 2300 has been removed. They guide cannulas 2304a and 2304b are held securely in place by the needle assemblies 2302a and 2302b, respectively, which are anchored into the bone. Additional guide cannulas (not shown) may be placed radially round the guide cannula 2304a be securing a needle targeting guide 2300 to the guide cannula 2304a as shown in FIGS. 28 and 29.

The first and second needle assemblies 2302a and 2302b, respectively, are similar to the first needle assembly 1252a illustrated in FIG. 20. A needle cannula assembly similar to the needle cannula assembly 2004 is used with guide cannulas 2304a and 2304b and needle targeting guide 2300. A drilling assembly similar to the drilling assembly 2002 is used with the needle cannula assembly and the needle targeting guide 2300.

In conclusion, the present invention includes: (1) the development of a minimally invasive method to wash out dead cells and necrotic fat materials from the marrow to improve bone healing, (2) the ability to lower the pressure of injection and minimize leakage of therapeutic agents, and (3) the ability to increase the distribution of therapeutic agents.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A surgical instrument for washing a bone marrow comprising:
   a handle;
   a central stationary assembly coupled to the handle, comprising a first guide cannula, a clamping mechanism, a first depth adjustment, and a first protractor arm component;
   a first needle assembly disposed to be inserted into, and end in the bone marrow at a first location, and wherein the first needle assembly is inserted into the first guide cannula and comprising a first needle assembly cannula, a first drilling assembly disposed to be inserted in the first needle assembly cannula, and a first locking mechanism disposed to engage the first drill assembly;
   an adjustable subassembly disposed to be rotatably coupled to the central stationary assembly and comprising a second guide cannula disposed to engage the clamping mechanism, a second depth adjustment, and a second protractor arm component disposed to slidably engage the first protractor arm component; and
   a second needle assembly disposed to be inserted into, and end in the bone marrow at a second location, wherein the first and second locations are separated by the bone marrow to be washed, and the second needle assembly is inserted into the second guide cannula and comprising a second needle assembly cannula, a second drilling assembly disposed to be inserted in the second needle assembly cannula, and a second locking mechanism disposed to engage the second drilling assembly, wherein the first needle assembly and the second needle assembly do not intersect and wherein the first needle assembly cannula is adapted to injected a fluid into the bone marrow that washes the bone marrow to remove dead cell debris, necrotic marrow fat, necrotic extracellular matrix and inflammatory factors from the bone marrow through the second needle assembly cannula.

2. The surgical instrument of claim 1, wherein the first locking mechanism comprises a first luer lock and a first luer lock collar disposed to engage the first luer lock.

3. The surgical instrument of claim 1, wherein the second locking mechanism comprises a second luer lock and a second luer lock collar disposed to engage the second luer lock.

4. The surgical instrument of claim 1, wherein the first locking mechanism comprises a first luer lock and a first drill interface disposed to rotatably engage the first luer lock.

5. The surgical instrument of claim 1, wherein the second locking mechanism comprises a second luer lock and a second drill interface disposed to rotatably engage the second luer lock.

6. The surgical instrument of claim 1, wherein the clamping mechanism comprises a guide clamp disposed to engage the second guide cannula, a tension clamp, and a tension clamp lever.

7. The surgical instrument of claim 1, wherein the first protractor arm component is disposed to slide on or within the second protractor arm component to position a first tip of the first needle assembly relative to a second tip of the second needle assembly when the first needle assembly is inserted into the first guide cannula and the second needle assembly is inserted into the second guide cannula.

8. A surgical instrument for washing bone marrow comprising:
   a frame with one or more locking pins disposed within the frame, wherein the frame is configured to receive a first guide cannula and a second guide cannula;
   the first guide cannula and the second guide cannula, wherein the first guide cannula and the second guide cannula are disposed to be inserted into the frame and locked into place with the one or more locking pins;
   a first needle assembly disposed to be inserted into, and end in the bone marrow at a first location, and wherein the first needle assembly is inserted into the first guide cannula and comprising a first needle assembly cannula, a first drilling assembly disposed to be inserted in the first needle cannula assembly, and a first locking mechanism disposed to engage the first drill assembly; and
   a second needle assembly disposed to be inserted into, and end in the bone marrow at a second location, wherein the first and second locations are separated by the bone marrow to be washed, and the second needle assemble is inserted into the second guide cannula and comprising a second needle assembly cannula, a second drilling assembly disposed to be inserted in the second needle assembly cannula, and a second locking mechanism disposed to engage the second drilling assembly, wherein the first needle assembly and the second needle assembly do not intersect and wherein the first needle assembly cannula is adapted to injected a fluid into the bone marrow that washes the bone marrow to remove at least one of dead cell debris, necrotic marrow fat, necrotic extracellular matrix or inflammatory factors from the bone marrow through the second needle assembly cannula.

9. The surgical instrument of claim 8, wherein the first locking mechanism comprises a first luer lock and a first luer lock collar disposed to engage the first luer lock.

10. The surgical instrument of claim 8, wherein the second locking mechanism comprises a second luer lock and a second luer lock collar disposed to engage the second luer lock.

11. The surgical instrument of claim 8, wherein the first locking mechanism comprises a first luer lock and a first drill interface disposed to rotatably engage the first luer lock.

12. The surgical instrument of claim 8, wherein the second locking mechanism comprises a second luer lock and a second drill interface disposed to rotatably engage the second luer lock.

* * * * *

UNITED STATES PATENT AND TRADEMARK OFFICE
CERTIFICATE OF CORRECTION

| | |
|---|---|
| PATENT NO. | : 10,765,453 B2 |
| APPLICATION NO. | : 15/956245 |
| DATED | : September 8, 2020 |
| INVENTOR(S) | : Harry K. W. Kim |

It is certified that error appears in the above-identified patent and that said Letters Patent is hereby corrected as shown below:

On the Title Page

Item (12) "Kim" should read --Kim et al--; and

Item (72) Inventor: should read as follows:
--(72) Inventors: Harry K. W. Kim, Dallas, TX (US); Brad Niese, Southlake, TX (US)--.

Signed and Sealed this
Thirty-first Day of May, 2022

Katherine Kelly Vidal
*Director of the United States Patent and Trademark Office*